(12) United States Patent
Riordan

(10) Patent No.: US 10,987,381 B2
(45) Date of Patent: Apr. 27, 2021

(54) MESENCHYMAL STEM CELLS WITH ENHANCED EFFICACY IN TREATMENT OF AUTOIMMUNITY PARTICULARLY RHEUMATOID ARTHRITIS

(71) Applicant: Neil Riordan, Westlake, TX (US)

(72) Inventor: Neil Riordan, Westlake, TX (US)

(*) Notice: Subject to any disclaimer, the term of this patent is extended or adjusted under 35 U.S.C. 154(b) by 295 days.

(21) Appl. No.: 15/882,904

(22) Filed: Jan. 29, 2018

(65) Prior Publication Data

US 2018/0214489 A1    Aug. 2, 2018

Related U.S. Application Data

(60) Provisional application No. 62/451,584, filed on Jan. 27, 2017.

(51) Int. Cl.
| | |
|---|---|
| *A61K 35/28* | (2015.01) |
| *A61P 37/06* | (2006.01) |
| *G01N 33/50* | (2006.01) |
| *G01N 33/68* | (2006.01) |
| *G01N 33/569* | (2006.01) |

(52) U.S. Cl.
CPC .............. *A61K 35/28* (2013.01); *A61P 37/06* (2018.01); *G01N 33/5005* (2013.01); *G01N 33/56966* (2013.01); *G01N 33/6863* (2013.01); *G01N 2800/24* (2013.01); *G01N 2800/38* (2013.01)

(58) Field of Classification Search
CPC ..... A61K 35/28; A61P 37/06; G01N 2800/24; G01N 2800/38; G01N 33/5005; G01N 33/56966; G01N 33/6863
See application file for complete search history.

(56) References Cited

U.S. PATENT DOCUMENTS

| | | | | |
|---|---|---|---|---|
| 2005/0239897 A1* | 10/2005 | Pittenger | ................ | A61K 35/28 514/569 |
| 2007/0020230 A1* | 1/2007 | Kaps | .................... | A61K 38/195 424/85.1 |
| 2009/0324609 A1* | 12/2009 | Lodie | ........................ | A61P 3/10 424/158.1 |
| 2010/0172885 A1* | 7/2010 | Pittenger | ................ | A61P 35/00 424/93.7 |
| 2011/0262402 A1* | 10/2011 | Kuroda | .................. | A61K 35/28 424/93.7 |
| 2012/0164114 A1* | 6/2012 | Abbot | ..................... | A61P 11/06 424/93.7 |
| 2012/0201791 A1* | 8/2012 | Yoo | ......................... | A61P 11/06 424/93.7 |
| 2015/0104470 A1* | 4/2015 | Riordan | ................. | A61K 35/17 424/184.1 |

* cited by examiner

*Primary Examiner* — Blaine Lankford
(74) *Attorney, Agent, or Firm* — Baumgartner Patent Law; Marc Baumgartner

(57) ABSTRACT

Disclosed herein are protocols, isolation means, and compositions of matter useful for identifying mesenchymal stem cells possessing enhanced clinical activity in treatment of autoimmune conditions, such as rheumatoid arthritis (RA). Additionally, markers associated with said enhanced mesenchymal stem cell activity against autoimmunity can be utilized to identify donors whose mesenchymal stem cells possess superior efficacy compared to mesenchymal stem cells from donors who lack said markers associated with said enhanced efficacy in treatment of autoimmunity, such as RA.

10 Claims, No Drawings

MESENCHYMAL STEM CELLS WITH ENHANCED EFFICACY IN TREATMENT OF AUTOIMMUNITY PARTICULARLY RHEUMATOID ARTHRITIS

CROSS-REFERENCE TO RELATED APPLICATIONS

The present invention claims priority to U.S. Provisional Application No. 62/451,584, filed Jan. 27, 2017, which is hereby incorporated in its entirety including all tables, figures, and claims.

FIELD OF THE INVENTION

The invention pertains to the area of stem cell therapeutics for the treatment of rheumatoid arthritis (RA), more specifically, the invention pertains to the area of mesenchymal stem cell therapeutics useful in the treatment of RA, more specifically, the invention pertains to means of selecting stem cells possessing enhanced efficacy for treatment of RA, furthermore the invention pertains to the area of stem cell efficacy markers useful for the treatment of RA.

BACKGROUND

The immune response is known to possess incredible efficacy at neutralizing microscopic pathogens, whether bacteria, parasitic or viral, and to some extent cancer cells. In general, the complicated mechanisms for self-recognition are efficient and allow a strong response to be directed exclusively at eliminating foreign antigens. The regulation of self/non-self discrimination, which is a critical function of the immune system, involves multiple mechanisms during the development and lifespan of adaptive immune cells such as T and B lymphocytes, as well as "semi-adaptive" immune cells such as NKT cells, gamma delta T cells, and NK cells [1].

An unfortunate medical reality is that in some situations, the immune system occasionally malfunctions and turns against the cells of the host thereby provoking an autoimmune response. Autoimmunity typically occurs when antigen receptors on immune cells recognize specific self-antigens on host cells and initiate reactions that result in the destruction of the host cells. In some instances, the autoreactive lymphocytes survive longer and continue to induce apoptosis or otherwise eliminate host cells causing autoimmune diseases. Different mechanisms have been described that prevent T lymphocytes from attacking self. These tolerance mechanisms act both on developing and mature T cells. For example, thymic positive selection skews the T cell repertoire to recognize self-MHC molecules and thus also enriches for auto-reactive T cells [2, 3]. On the other hand, thymic negative selection, which follows positive selection, eliminates auto-reactive T cells either by clonal deletion (death) or inactivation, (anergy). Whereas clonal deletion deals with high affinity T cells at the CD4+CD8+ TCR.sup.high maturation stage, clonal inactivation seems to work at lower affinity interaction possibly by the down-regulation of the TCR and the CD8.alpha.-chain. However, these "anergic" T lymphocytes still have the ability to specifically respond to their antigen. It has been suggested that they actually might represent a population of regulatory T cells since they release IL-10 and TGF-.beta. upon stimulation. Thus, it is well-established that thymic (central) tolerance mechanisms do not eliminate all autoreactive T cells. Indeed, T cells reactive with self-antigens, such as myelin basic protein (MBP), insulin and glutamic acid decarboxylase (GAD), can be readily found in the periphery.

In patients with certain genetic abnormalities or predispositions, the tolerogenic processes do not possess full ability to prevent autoreactivity, and when combined with proper stimulation, tolerance to self is broken and pathology ensues. The induction of autoimmunity is associated with various immunological cells interacting and consistently overcoming tolerogenic processes. Both CD4+ helper T cells as well as CD8+ cytotoxic T cells (CTLs) play important roles in the autoantigen immune response. In the well-accepted NOD mouse model of spontaneous diabetes, for example, both CD4+ and CD8+ T cells are crucial for disease development. Directly- and indirectly-primed CD4+ T cells help in the production of autoantibody and provide the signals required for induction of CD8+ CTLs, both of which are capable of injuring the cells expressing the autoantigen. Thus, the success of any immunosuppressive strategy directed against an autoimmune response depends on the effective inhibition of both major subsets of T cells.

Existing treatments for autoimmune diseases have had only limited success. For example, it is often possible to correct organ-specific autoimmune disease through metabolic control. Where function is lost and cannot be restored, mechanical substitutes or tissue grafts may be appropriate. While it may be possible to alleviate some of the symptoms using this approach, no effective long-term curative treatment exists for several of the most disabling autoimmune disorders, including multiple sclerosis and insulin-dependent diabetes mellitus (IDDM). While a number of compounds, including insulin, corticosteroids and modified beta interferon can ameliorate some of the symptoms of autoimmune diseases, they can have serious side effects and/or require long-term use. General immunosuppressive drug therapies, such as chronic treatment with cyclosporin A, FK506 and rapamycin have also been unable to provide a cure for these diseases, and their use is accompanied by a host of deleterious side effects. Said effects include nephrotoxicity, increased predisposition to infectious diseases, and enhanced incidence of neoplasia.

A more advanced approach to treatment of autoimmunity is the use of immune modulatory strategies that are antigen-specific. Examples that have been proposed based on the systemic administration of DNA vaccines encoding autoantigens, either alone or in combination with T-helper type 2 (Th2) cytokines such as IL-4 and IL-10. U.S. Patent Publication No. US 2003/0148983 A1, the disclosures of which are expressly incorporated by reference herein. The preliminary data reported by these researchers suggested that DNA vaccines encoding the autoantigen alone could potentially anergize autoreactive T cells, while tolerizing vaccines in combination with IL-4 could help induce Th2 responses, which in numerous autoimmune conditions are known to be inhibitory to pathology, which is classically associated with Th1/Th17 cells. Data from another group of researchers suggested that the presence of IL-4 was critical for protection against disease development induced by the tolerizing vaccine. Thus, the success of this therapeutic strategy likely hinges on the co-administration of Th2-associated cytokines or vectors encoding the same along with the tolerizing vaccine to bias a pro-inflammatory T-helper type 1 (Th1) response to more protective Th2 response. Although this vaccine-based strategy has been somewhat effective in a prophylactic setting, it may prove much more difficult to treat an active autoimmune response already heavily biased towards an inflammatory Th1 response.

Accordingly, novel therapeutic compositions and protocols are sought that can inhibit the function of autoreactive T cells, including Th1-type T cells, in a highly specific fashion. It is an object of the present invention to inhibit and/or eliminate autoreactive CD4+ and CD8+ T lymphocytes to prevent the development of, as well as the progression of, autoimmune diseases.

Rheumatoid arthritis (RA) is a chronic inflammatory disorder affecting approximately 0.5-1% of the global population [4], characterized by immune-mediated synovial inflammation and joint deterioration. In general, because of the critical role of inflammation in the pathology of RA, patients have usually been started on NSAIDS, however more recent practice has been concurrent initiation of disease modifying antirheumatic drugs (DMARDs). These agents are slow acting but have been demonstrated to inhibit radiological progression of RA. Such agents typically include: 1) hydroxychloroquine, which acts in part as a toll like receptor (TLR) 7/9 antagonist, thus decreasing innate immune activation [5]; 2) Leflunomide, an antimetabolite that inhibits pyrimidine synthesis and protein tyrosine kinase activity [6], which results in suppression of T cell responses [7], and has been also demonstrated to inhibit dendritic cell (DC) activation [8]; 3) Injectable gold compounds such as auranofin which directly or through metabolites such as dicyanogold(i) have been demonstrated to inhibit T cell and antigen presenting cell activation [9, 10], as well as cause Th2 deviation [11]; 4) Sulfasalazine, was used since 1950, acts primarily through inhibition of cycloxygenase and lipoxygenase [12]; and 5) Methotrexate, an antifolate that inhibits T cell activation and proliferation, that has been one of the golden standards for RA [13]. Typically combinations of DMARDs with glucocorticoids are used, or alternatively pulse of high dose glucocorticoids are administered to cause a general inhibition of inflammation [14].

The TNF-alpha targeting agents, Remicade, Enbrel, and Humira, sometimes referred to as "biological DMARDs" are used primarily after response to conventional DMARDs has failed [15]. Although improvement in quality of life has occurred as a result of biological DMARDs, substantial progress remains to be made. For example, TNF-alpha blockers have been associated with reactivation of infectious disease, autoantibody formation and the possibility of increased lymphoma risk [16, 17]. Thus to date, one of the major limitations to RA therapy has been lack of ability to specifically inhibit autoreactive responses while allowing other immune components to remain intact.

SUMMARY

The inventions herein is directed to the following embodiments:
1. A method of selecting for mesenchymal stem cells possessing enhanced efficacy against autoimmunity, said method comprising the steps of: a) obtaining a group of mesenchymal stem cells; b) identifying expression of one or more markers selected from a group comprising of TNFR-1, ENA-78, and IGFBP-3; c) selecting for cells that express higher levels of one or more proteins selected from a group comprising of TNFR-1, ENA-78, and IGFBP-3.
2. The method of claim 1, wherein said mesenchymal stem cells are naturally occurring mesenchymal stem cells.
3. The method of claim 1, wherein said mesenchymal stem cells are generated in vitro.
4. The method of claim 2, wherein said naturally occurring mesenchymal stem cells are tissue derived.
5. The method of claim 2, wherein said naturally occurring mesenchymal stem cells are derived from a bodily fluid.
6. The method of claim 4, wherein said tissue derived mesenchymal stem cells are selected from a group comprising of: a) bone marrow; b) perivascular tissue; c) adipose tissue; d) placental tissue; e) amniotic membrane; f) omentum; g) tooth; h) umbilical cord tissue; i) fallopian tube tissue; j) hepatic tissue; k) renal tissue; l) cardiac tissue; m) tonsillar tissue; n) testicular tissue; o) ovarian tissue; p) neuronal tissue; q) auricular tissue; r) colonic tissue; s) submucosal tissue; t) hair follicle tissue; u) pancreatic tissue; v) skeletal muscle tissue; and w) subepithelial umbilical cord tissue.
7. The method of claim 4, wherein said tissue derived mesenchymal stem cells are isolated from tissues containing cells selected from a group of cells comprising of: endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus *luteum* cells, granulosa lutein cells, theca lutein cells, juxtaglomerular cell, macula *densa* cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

8. The method of claim 1, wherein said mesenchymal stem cells are plastic adherent.

9. The method of claim 1, wherein said mesenchymal stem cells express a marker selected from a group comprising of: a) CD73; b) CD90; and c) CD105.

10. The method of claim 1, wherein said mesenchymal stem cells lack expression of a marker selected from a group comprising of: a) CD14; b) CD45; and c) CD34.

11. The method of claim 6, wherein said mesenchymal stem cells from umbilical cord tissue express markers selected from a group comprising of; a) oxidized low density lipoprotein receptor 1, b) chemokine receptor ligand 3; and c) granulocyte chemotactic protein.

12. The method of claim 6, wherein said mesenchymal stem cells from umbilical cord tissue do not express markers selected from a group comprising of: a) CD117; b) CD31; c) CD34; and CD45;

13. The method of claim 6, wherein said mesenchymal stem cells from umbilical cord tissue express, relative to a human fibroblast, increased levels of interleukin 8 and reticulon 1

14. The method of claim 6, wherein said mesenchymal stem cells from umbilical cord tissue have the potential to differentiate into cells of at least a skeletal muscle, vascular smooth muscle, pericyte or vascular endothelium phenotype.

15. The method of claim 6, wherein said mesenchymal stem cells from umbilical cord tissue express markers selected from a group comprising of: a) CD10; b) CD13; c) CD44; d) CD73; and e) CD90.

16. The method of claim 6, wherein said umbilical cord tissue mesenchymal stem cell is an isolated umbilical cord tissue cell isolated from umbilical cord tissue substantially free of blood that is capable of self-renewal and expansion in culture, 17. The method of claim 16, wherein said umbilical cord tissue mesenchymal stem cells has the potential to differentiate into cells of other phenotypes.

18. The method of claim 17, wherein said other phenotypes comprise: a) osteocytic; b) adipogenic; and c) chondrogenic differentiation.

19. The method of claim 6, wherein said cord tissue derived mesenchymal stem cells can undergo at least 20 doublings in culture.

20. The method of claim 6, wherein said cord tissue derived mesenchymal stem cell maintains a normal karyotype upon passaging 21. The method of claim 6, wherein said cord tissue derived mesenchymal stem cell expresses a marker selected from a group of markers comprised of: a) CD10 b) CD13; c) CD44; d) CD73; e) CD90; f) PDGFr-alpha; g) PD-L2; and h) HLA-A, B, C 22. The method of claim 6, wherein said cord tissue mesenchymal stem cells does not express one or more markers selected from a group comprising of; a) CD31; b) CD34; c) CD45; d) CD80; e) CD86; f) CD117; g) CD141; h) CD178; i) B7-H2; j) HLA-G and k) HLA-DR, DP, DQ.

23. The method of claim 6, wherein said umbilical cord tissue-derived cell secretes factors selected from a group comprising of: a) MCP-1; b) MIP1beta; c) IL-6; d) IL-8; e) GCP-2; f) HGF; g) KGF; h) FGF; i) HB-EGF; j) BDNF; k) TPO; l) RANTES; and m) TIMP1

24. The method of claim 6, wherein said umbilical cord tissue derived cells express markers selected from a group comprising of: a) TRA1-60; b) TRA1-81; c) SSEA3; d) SSEA4; and e) NANOG.

25. The method of claim 6, wherein said umbilical cord tissue-derived cells are positive for alkaline phosphatase staining.

26. The method of claim 6, wherein said umbilical cord tissue-derived cells are capable of differentiating into one or more lineages selected from a group comprising of; a) ectoderm; b) mesoderm, and; c) endoderm.

27. The method of claim 6, wherein said bone marrow derived mesenchymal stem cells possess markers selected from a group comprising of: a) CD73; b) CD90; and c) CD105.

28. The method of claim 6, wherein said bone marrow derived mesenchymal stem cells possess markers selected from a group comprising of: a) LFA-3; b) ICAM-1; c) PECAM-1; d) P-selectin; e) L-selectin; f) CD49b/CD29; g) CD49c/CD29; h) CD49d/CD29; i) CD29; j) CD18; k) CD61; l) 6-19; m) thrombomodulin; n) telomerase; o) CD10; p) CD13; and q) integrin beta.

29. The method of claim 6, wherein said bone marrow derived mesenchymal stem cell is a mesenchymal stem cell progenitor cell.

30. The method of claim 29, wherein said mesenchymal progenitor cells are a population of bone marrow mesenchymal stem cells enriched for cells containing STRO-1

31. The method of claim 30, wherein said mesenchymal progenitor cells express both STRO-1 and VCAM-1.

32. A method of claim 30, wherein said STRO-1 expressing cells are negative for at least one marker selected from the group consisting of: a) CBFA-1; b) collagen type II; c) PPAR.gamma2; d) osteopontin; e) osteocalcin; f) parathyroid hormone receptor; g) leptin; h) H-ALBP; i) aggrecan; j) Ki67, and k) glycophorin A.

33. The method of claim 6, wherein said bone marrow mesenchymal stem cells lack expression of CD14, CD34, and CD45.

34. The method of claim 32, wherein said STRO-1 expressing cells are positive for a marker selected from a group comprising of: a) VACM-1; b) TKY-1; c) CD146 and; d) STRO-2

35. The method of claim 6, wherein said bone marrow mesenchymal stem cell express markers selected from a group comprising of: a) CD13; b) CD34; c) CD56 and; d) CD117

36. The method of claim 35, wherein said bone marrow mesenchymal stem cells do not express CD10.

37. The method of claim 35, wherein said bone marrow mesenchymal stem cells do not express CD2, CD5, CD14, CD19, CD33, CD45, and DRII.

38. The method of claim 35, wherein said bone marrow mesenchymal stem cells express CD13, CD34, CD56, CD90, CD117 and nestin, and which do not express CD2, CD3, CD10, CD14, CD16, CD31, CD33, CD45 and CD64.

39. The method of claim 6, wherein said skeletal muscle stem cells express markers selected from a group comprising of: a) CD13; b) CD34; c) CD56 and; d) CD117

40. The method of claim 40, wherein said skeletal muscle mesenchymal stem cells do not express CD10.

41. The method of claim 40, wherein said skeletal muscle mesenchymal stem cells do not express CD2, CD5, CD14, CD19, CD33, CD45, and DRII.

42. The method of claim 40, wherein said bone marrow mesenchymal stem cells express CD13, CD34, CD56, CD90, CD117 and nestin, and which do not express CD2, CD3, CD10, CD14, CD16, CD31, CD33, CD45 and CD64.

43. The method of claim 6, wherein said subepithelial umbilical cord derived mesenchymal stem cells possess markers selected from a group comprising of; a) CD29; b) CD73; c) CD90; d) CD166; e) SSEA4; 0 CD9; g) CD44; h) CD146; and i) CD105

44. The method of claim 43, wherein said subepithelial umbilical cord derived mesenchymal stem cells do not express markers selected from a group comprising of; a) CD45; b) CD34; c) CD14; d) CD79; e) CD106; f) CD86; g) CD80; h) CD19; i) CD117; j) Stro-1 and k) HLA-DR.

45. The method of claim 43, wherein said subepithelial umbilical cord derived mesenchymal stem cells express CD29, CD73, CD90, CD166, SSEA4, CD9, CD44, CD146, and CD105.

46. The method of claim 43, wherein said subepithelial umbilical cord derived mesenchymal stem cells do not express CD45, CD34, CD14, CD79, CD106, CD86, CD80, CD19, CD117, Stro-1, and HLA-DR.

47. The method of claim 43, wherein said subepithelial umbilical cord derived mesenchymal stem cells are positive for SOX2.

48. The method of claim 43, wherein said subepithelial umbilical cord derived mesenchymal stem cells are positive for OCT4.

49. The method of claim 43, wherein said subepithelial umbilical cord derived mesenchymal stem cells are positive for OCT4 and SOX2.

50. The method of claim 1, wherein said efficacy reflects enhanced ability to inhibit pathological immunity.

51. The method of claim 1, wherein said efficacy reflects enhanced ability to inhibit Th17 cell generation.

52. The method of claim 1, wherein said efficacy reflects enhanced ability to stimulate endogenous regenerative activity.

53. The method of claim 1, wherein said efficacy reflects enhanced ability to induce T regulatory cells.

54. The method of claim 1, wherein said efficacy reflects enhanced ability to induce clinical response in a disease condition.

55. The method of claim 54, wherein said autoimmune condition is rheumatoid arthritis.

56. The method of claim 1, wherein said mesenchymal stem cells selected for enhanced efficacy are utilized as a source of conditioned media.

57. The method of claim 56, wherein conditioned media is used therapeutically in the treatment of a disorder.

58. The method of claim 57, wherein said autoimmune disorder is selected from a group comprising of a) rheumatoid arthritis; b) multiple sclerosis; c) Type 1 diabetes; d) myocarditis; e) pathological immunity towards blood vessels; f) scleroderma; g) psoriasis; h) Crohn's disease; i) colitis; j) autoimmune gastritis; k) Hashimoto's thyroiditis; l) Sjorden's Disease; m) Oochritis; n) ocular autoimmunity; o) aplastic anemia; p) premature ovarian failure; q) primary biliary cirrhosis; r) autism; s) chronic fatigue syndrome; t) Lyme's disease; u) transplant rejection; and v) autoimmune myopathies.

59. The method of claim 1, wherein mesenchymal stem cells are selected for enhanced efficacy by selecting for cells expressing higher levels of one more proteins selected from a group comprising of TNFR-1, ENA-78, and IGFBP-3.

60. The method of claim 1, wherein mesenchymal stem cells are selected for enhanced efficacy by selecting for cells expressing higher levels of TNFR-1, ENA-78, and IGFBP-3.

61. The method of claim 1, wherein selection of cells for high or low expression of markers is performed by flow cytometry sorting.

62. The method of claim 61, wherein said flow cytometry sorting is performed by utilizing a fluorescent means that selectively induces a signal upon binding to markers of said cells.

63. The method of claim 62, wherein said flow cytometry sorting is performed by utilizing a fluorescent means that selectively induces a signal upon alteration induced by markers in said mesenchymal stem cells.

64. The method of claim 63, wherein said alteration induced by said marker is an enzymatic interaction.

DESCRIPTION OF THE INVENTION

The invention teaches means of selecting stem cells for treatment of autoimmune conditions, based on variability of stem cells from different donors, as well as markers associated with efficacy. In one particular embodiment the invention teaches means of selecting positively, and/or negatively for enhanced activity against autoimmunity, in more particular, the invention teaches means of selecting for mesenchymal stem cells (MSC) that have enhanced activity for the treatment of RA. MSC therapeutics are well known in the art. These cells have entered the clinical arena in the treatment of various degenerative conditions including cardiovascular, neurological, and immunological. Regulatory approval of mesenchymal stem cell based products has been achieved in several jurisdictions, particularly of mesenchymal stem cells. The classical description of MSC are adherent cells possessing ability to differentiate into osteoblasts, adipocytes and chondrocytes and possessing the surface markers CD73, CD90, and CD105, while lacking the markers CD14, CD34, and CD45.

There are factors that are known to affect the therapeutic efficacy of MSC therapy, in particular selection of donors for generation of mesenchymal stem cell therapy appears to be a major factor in whether such therapy will be efficacious. Although criteria such as young donor age and absence of chronic disease, is utilized by some as a means of selecting donors with enhanced efficacy, to date, no consistent means of selecting donors based on markers exists that has been validated in a clinical setting. In view of the foregoing, there exists a need in the art for providing and/or developing an alternative strategy that; a) allows for selection of mesenchymal stem cells with enhanced efficacy against autoimmune conditions, with particular emphasis in this current disclosure; and b) allows for selection of donors whose MSC possess enhanced efficacy from an anti-rheumatic perspective.

The invention teaches means of selecting MSC for enhanced efficacy based on expression, or lack of expression of certain proteins. In one particular embodiment, MSC are generated from a series of MSC donors, with each donor representing a lot of MSC. Said lots are screened for enhanced efficacy based on expression of markers selected from a group comprising of TNFR-1, ENA-78, and IGFBP-3. Furthermore, within the practice of the invention MSC donor lots are selected for reduced expression of markers TNFR-1, ENA-78, and IGFBP-3. In one preferred embodiment MSC donor lots are selected for both enhanced expression of one or more proteins selected from a group comprising of TNFR-1, ENA-78, and IGFBP-3 as compared to comparator donor lots. MSC sources are known in the literature and can be derived from tissue, or bodily fluids.

The invention teaches that MSC of various origin can be selected for higher ability to inhibit clinical progression, stabilize disease activity, or reverse disease activity in the context of autoimmunity, or in specific embodiments, rheumatoid arthritis (RA). In one embodiment the invention teaches the selection of MSC, either based on markers found in specific donors which naturally possess higher levels of markers associated with activity, or selecting for cells which have higher expression of MSC markers associate with activity. Said activity culminates in enhanced clinical activity but without being reduced to theory, enhanced ability to inhibit the pathological response through "reprogramming" of immune effectors.

In some specific embodiments the invention teaches the systemic administration of MSC with enhanced activity alone. In other embodiments the invention provides the administration of MSC together with autoantigens. Said autoantigens associated with RA include the extracellular matrix protein collagen II. Demonstration of the immunological significant of collagen II is shown by induction of a RA-like disease which has been reported in inbred strains following immunization of collagen II in the presence of adjuvant [18]. Autoimmunity was not induced by collagen I or III, nor by denatured collagen II protein. Supporting a causative immunopathological effect of collagen II specific T cells were experiments in which the RA-like disease could be transferred to naïve recipients by administration of lymph node cells [19]. Subsequent work cloning T cell lines from synovial membranes of patients with RA demonstrated existence of collagen II-specific cells that persisted for a period of 3 years in vivo [20]. Subsequent PCR-studies of T cell receptor beta chains confirmed the oligoclonal expansion of collagen II-reactive cells in patients [21]. In 1993 Weiner's group reported a double blind, placebo-controlled trial of 60 patients with advanced RA treated by oral administration of chicken collagen II for a period of 3 months. Responses in terms of decreased number of swollen joints were observed in the treated population but not placebo controls. Of the treated patients four presented with complete remission of disease. No treatment-associated adverse effects were noted [22]. Unfortunately, Phase III trials using oral tolerance in RA have not met primary efficacy endpoints [23]. In one embodiment tolerogenic activity of collagen II administration by oral or other means is augmented by co-administration of said antigen together with MSC possessing enhanced activity.

Given the general failure of oral tolerance in RA, more specific approaches have involved stimulation of tolerogenic responses using ex vivo manipulated DC. Dendritic cells (DC) under physiological conditions promote tolerance, and when exposed to injury/damage signals mature and induce T cell activation. By ex vivo manipulating antigen pulsed/donor specific DC, we have previously been able to induce antigen-specific suppression of immunity and generation of T regulatory (Treg) cells. Tolerogenic modifications of DC performed by our group have included exposure of the DC to small molecule immune suppressants [24-26], gene transfection with tolerogenic genes [27, 28] and gene silencing of immune activatory genes [29-32]. In our previous work, we have demonstrated ability to prevent RA induction by pulsing DC with collagen II (CII) and suppressing DC maturation with chemical or genetic means. Limitations of these data, however, have been the lack of robust inhibition of inflammatory responses when administration of manipulated DC was performed at various time points subsequent to disease onset. MSC are known to inhibit DC maturation, accordingly, in one embodiment MSC selected for enhanced anti-autoimmune activity are cocultured with antigen-pulsed DC and administered. In another embodiment, enhanced MSC are administered locally into areas in which immature antigen-pulsed DC are administered or are known to migrate to. Said areas include lymph nodes or areas draining into lymph nodes. In another embodiment enhanced MSC are administered systemically, as are immature DC that are pulsed with antigen.

Theoretically, MSC appear to possess advantages to other antigen-specific and non-specific immune modulatory approaches. One such advantage is that the MSC may be viewed as a "intelligent" immune modulators. In contrast to current therapies, which globally cause immune suppression, production of anti-inflammatory factors by MSC appears to be dependent on their environment, with upregulation of factors such as TGF-b, HLA-G, IL-10, and neuropilin-A ligands galectin-1 and Semaphorin-3A in response to immune/inflammatory stimuli but little in the basal state [33-37]. This property may be selected for when utilizing the marker combinations disclosed in the current invention.

Additionally, systemically administered MSC possess ability to selectively home to injured/hypoxic areas by recognition of signals such as HMGB1 or CXCR1, respectively [38-41]. The ability to home to injury, combined with selective induction of immune modulation only in response to inflammatory/danger signals suggests the possibility that systemically administered MSC do not cause global immune suppression. This is supported by clinical studies using MSC for other inflammatory conditions, which to date, have not reported immune suppression associated adverse effects

[42-44]. Another important aspect of MSC therapy is their ability to regenerate injured tissue through direct differentiation into articular tissue [45], as well as ability to secret growth factors capable of augmenting endogenous regenerative processes [46]. These properties may be utilized in the practice of the current invention by selecting for cells of the MSC lineage which possess markers associated with enhanced clinical activity, such as reduction, stabilization or inhibition of arthritis score progression.

The importance of selecting for specific MSC types or donors can be illustrated in studies in which MSC administration actually accelerated pathology. The concept of MSC contributing to pathology was demonstrated in the CIA model by Djouad et al who reported administration of MSC resulted in upregulation of Th1 immunity and worsening of symptoms [47]. The investigators attributed this to their observations that TNF-alpha abrogates immune regulatory activities of MSC. This study however was contradicted by several more recent studies in which inhibition of arthritogenesis, or even regression of disease was observed. Mao et al demonstrated administration of rat MSC intravenously into DBA mice with full-blow CIA resulted in regression of disease, which was correlated with decreased production of TNF-alpha and IL-17 [48]. Gonzalez et al administered ex vivo expanded human adipose-derived MSC into the same animal model. Inhibition of disease progression was observed, which correlated with increased Treg numbers that were specific for CII. This study supports the previous principle discussed that an antigen-nonspecific tolerizing event may contribute to development of antigen specific suppression [49]. In addition to immune modulation, it is possible that cartilage tissue generated de novo from MSC possesses a decreased level of immunogenicity [50]. The overall anti-inflammatory/immune modulatory effects of MSC have been demonstrated in a variety of settings including the mouse model of multiple sclerosis [51, 52], transplant rejection [53], diabetes [54], the mouse model of SLE [55], and autoimmune enteropathy [56]. These results support a variability of MSC efficacy depending on specific donors, or markers of subtypes of MSC.

For the practice of the invention, MSC with enhanced activity can be utilized as was previously performed in clinical trials with non-selected MSC. "Mesenchymal stem cell" or "MSC" in some embodiments refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage. Other cells possessing mesenchymal-like properties are included within the definition of "mesenchymal stem cell", with the condition that said cells possess at least one of the following: a) regenerative activity; b) production of growth factors; c) ability to induce a healing response, either directly, or through elicitation of endogenous host repair mechanisms. As used herein, "mesenchymal stromal cell" or ore mesenchymal stem cell can be used interchangeably. Said MSC can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and tooth. In some definitions of "MSC", said cells include cells that are CD34 positive upon initial isolation from tissue but are similar to cells described about phenotypically and functionally. As used herein, "MSC" may includes cells that are isolated from tissues using cell surface markers selected from the list comprised of NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 or any combination thereof, and satisfy the ISCT criteria either before or after expansion. Furthermore, as used herein, in some contexts, "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), MultiStem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, Stemedyne™-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs).

These studies are incorporated by reference in their entirety. One of the first studies was aimed to determine the safety and efficacy of allogeneic mesenchymal stem cells transplantation (MSCT) in refractory rheumatoid arthritis (RA). Four patients with persistently active RA underwent MSCT. The outcome was evaluated by changes in the visual analog scale (VAS 100 mm) pain score, C-reactive protein (CRP) and erythrocyte sedimentation rate (ESR), and 28-joint disease activity score (DAS-28). Three of four patients received a reduction in ESR, DAS-28, and pain VAS score at 1 and 6 months after transplantation. Two of the three had a European League Against Rheumatism (EULAR) moderate response at 6 months but experienced a relapse at 7 and 23 months, respectively. Two patients had no EULAR response to MSCT. No one had achieved the DAS-28-defined remission in the follow-up period. No serious adverse events were reported. It was reported that allogeneic MSCT is a safe treatment in severe and resistant RA, but the effectiveness needs to be clarified [57]. A subsequent study used human umbilical cord mesenchymal stem cells (UC-MSCs) in the treatment of rheumatoid arthritis (RA). In this ongoing cohort, 172 patients with active RA who had inadequate responses to traditional medication were enrolled. Patients were divided into two groups for different treatment: disease-modifying anti-rheumatic drugs (DMARDs) plus medium without UC-MSCs, or DMARDs plus UC-MSCs group (4×10(7) cells per time) via intravenous injection. Adverse events and the clinical information were recorded. Tests for serological markers to assess safety and disease activity were conducted. Serum levels of inflammatory chemokines/cytokines were measured, and lymphocyte subsets in peripheral blood were analyzed. No serious adverse effects were observed during or after infusion. The serum levels of tumor necrosis factor-alpha and interleukin-6 decreased after the first UC-MSCs treatment ($P<0.05$). The percentage of CD4(+)CD25(+)Foxp3(+) regulatory T cells of peripheral blood was increased ($P<0.05$). The treatment induced a significant remission of disease according to the American College of Rheumatology improvement criteria, the 28-joint disease activity score, and the Health Assessment Questionnaire. The therapeutic effects maintained for 3-6 months without continuous administration, correlating with the increased percentage of regulatory T cells of peripheral blood. Repeated infusion after this period can enhance the therapeutic efficacy. In comparison, there were no such benefits observed in control group of DMARDS plus medium without UC-MSCs. Thus, our data indicate that treatment with DMARDs plus UC-MSCs may provide safe, significant, and persistent clinical benefits for patients with active RA.[58]. Another UC-MSC trial aimed to treat juvenile idiopathic arthritis (JIA), known as Juvenile rheumatoid arthritis, is the most common type of arthritis in children aged under 17. It may cause sequelae due to lack of effective treatment. The goal of this study is to explore the therapeutic effect of umbilical cord mesenchymal stem cells (UC-MSCs) for JIA. Ten JIA patients were treated with UC-MSCs and received second infusion three months later. Some key values such as 28-joint disease activity score (DAS28), TNF-α, IL-6, and regulatory T cells (Tregs) were evaluated. Data were collected at 3 months and 6 months after first treatment. DAS28 score of 10 patients was between 2.6 and 3.2 at three months after infusion. WBC, ESR, and CRP were significantly decreased while Tregs were remarkably increased and IL-6 and TNF-α were declined. Similar changes of above values were found after 6 months. At the same time, the amount of NSAIDS and steroid usage in patients was reduced. However, no significant changes were found comparing the data from 3 and 6 months. These results suggest that UC-MSCs can reduce inflammatory cytokines, improve immune network effects, adjust immune tolerance, and effectively alleviate the symptoms and they might provide a safe and novel approach for JIA treatment [59].

An interesting perspective is the use of expanded allogeneic adipose MSC, which is also disclosed as an embodiment of the invention. Patients with active refractory RA (failure to at least two biologicals) were randomised to receive three intravenous infusions of Cx611: 1 million/kg (cohort A), 2 million/kg (cohort B), 4 million/kg (cohort C) or placebo, on days 1, 8 and 15, and they were followed for therapy assessment for 24 weeks. Fifty-three patients were treated (20 in cohort A, 20 in cohort B, 6 in cohort C and 7 in placebo group). A total of 141 adverse events (AEs) were reported. Seventeen patients from the group A (85%), 15 from the group B (75%), 6 from the group C (100%) and 4 from the placebo group (57%) experienced at least one AE.Eight AEs from 6 patients were grade 3 in intensity (severe), 5 in cohort A (lacunar infarction, diarrhoea, tendon rupture, rheumatoid nodule and arthritis), 2 in cohort B (sciatica and RA) and 1 in the placebo group (asthenia). Only one of the grade 3 AEs was serious (the lacunar infarction). American College of Rheumatology 20 responses for cohorts A, B, C and placebo were 45%, 20%, 33% and 29%, respectively, at month 1, and 25%, 15%, 17% and 0%, respectively, at month 3. The authors concluded that intravenous infusion of Cx611 was in general well tolerated, without evidence of dose-related toxicity at the dose range and time period studied. In addition, a trend for clinical efficacy was observed. These data, in our opinion, justify further investigation of this innovative therapy in patients with RA[60].

In one embodiment, the cells of the present invention are generally referred to as umbilical-derived cells (or UDCs). They also may sometimes be referred to more generally herein as postpartum-derived cells or postpartum cells (PPDCs). In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below.

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium. In one specific embodiment of the invention, supernatant is collected from MSC selected for enhanced activity. Said enhanced activity is identified based on proteomic and other analysis of markers, proteins, and peptides that are correlated with enhanced activity against autoimmune conditions. In a specific embodiment the invention provides means of immune modulating using said conditioned media. In some embodiments of the invention, the inventors interchangeably use the words "conditioned media" and "trophic factors". Generally, a trophic factor is defined as a substance that promotes or at least supports, survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown, continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth Medium generally refers to a medium sufficient for the culturing of umbilicus-derived cells. In particular, one presently preferred medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.).

The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium.

Also relating to the present invention, the term standard growth conditions, as used herein refers to culturing of cells at 37.degree. C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

"Enhanced MSC" refers to MSC or MSC-like cells that are selected for higher expression of one or more proteins selected from a group comprising of TNFR-1, ENA-78, and IGFBP-3. In a preferred embodiment "Enhanced MSC" are MSC or MSC-like cells that possess higher levels of a protein selected from a group comprising of TNFR-1, ENA-78, and IGFBP-3 as compared to other MSC in a culture population, or as compared to MSC derived from different donors.

Oct-4 (oct-3 in humans) is a transcription factor expressed in the pregastrulation embryo, early cleavage stage embryo, cells of the inner cell mass of the blastocyst, and embryonic carcinoma ("EC") cells (Nichols, J. et al. (1998) Cell 95: 379-91), and is down-regulated when cells are induced to differentiate. The oct-4 gene (oct-3 in humans) is transcribed into at least two splice variants in humans, oct-3A and oct-3B. The oct-3B splice variant is found in many differentiated cells whereas the oct-3A splice variant (also previously designated oct-3/4) is reported to be specific for the undifferentiated embryonic stem cell. See Shimozaki et al. (2003) Development 130: 2505-12. Expression of oct-3/4 plays an important role in determining early steps in embryogenesis and differentiation. Oct-3/4, in combination with rox-1, causes transcriptional activation of the Zn-finger protein rex-1, which is also required for maintaining ES cells in an undifferentiated state (Rosfjord, E. and Rizzino, A. (1997) Biochem Biophys Res Commun 203: 1795-802; Ben-Shushan, E. et al. (1998) Mol Cell Biol 18: 1866-78).

The term "neoplasm" generally denotes disorders involving the clonal proliferation of cells. Neoplasms may be benign, which is to say, not progressive and non-recurrent, and, if so, generally are not life-threatening. Neoplasms also may be malignant, which is to say, that they progressively get worse, spread, and, as a rule, are life threatening and often fatal.

The definition of "autoimmunity" within the context of the invention includes inflammatory conditions, whether or not they are triggered by a classical adaptive immune attack on self tissue Inflammatory conditions is an inclusive term and includes, for example: (1) tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; (2) inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membranous nephritis, and pancreatitis; (3) transplant rejection, e.g., hyperacute xenograft rejection; (4) pregnancy related diseases such as recurrent fetal loss and pre-eclampsia, and (5) adverse drug reactions, e.g., drug allergy, IL-2 induced vascular leakage syndrome and radiographic contrast media allergy. Complement-mediated inflammation associated with autoimmune disorders including, but not limited to, myasthenia gravis, Alzheimer's disease, multiple sclerosis, rheumatoid arthritis, systemic lupus erythematosus, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barre syndrome, Hashimoto's disease, idiopathic thrombocytopenic purpura, pemphigus, Sjogren's syndrome, and Takayasu's arteritis, may also be detected with the methods described herein.

In one embodiment MSC donor lots are generated from umbilical cord tissue. Means of generating umbilical cord tissue MSC have been previously published and are incorporated by reference [61-67]. The term "umbilical tissue derived cells (UTC)" refers, for example, to cells as described in U.S. Pat. Nos. 7,510,873, 7,413,734, 7,524,489, and 7,560,276. The UTC can be of any mammalian origin e.g. human, rat, primate, porcine and the like. In one embodiment of the invention, the UTC are derived from human umbilicus. umbilicus-derived cells, which relative to a human cell that is a fibroblast, a mesenchymal stem cell, or an iliac crest bone marrow cell, have reduced expression of genes for one or more of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeobox 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle). In addition, these isolated human umbilicus-derived cells express a gene for each of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3, wherein the expression is increased relative to that of a human cell which is a fibroblast, a mesenchymal stem cell, an iliac crest bone marrow cell, or placenta-derived cell. The cells are capable of self-renewal and expansion in culture, and have the potential to differentiate into cells of other phenotypes.

Methods of deriving cord tissue mesenchymal stem cells from human umbilical tissue are provided. The cells are capable of self-renewal and expansion in culture, and have the potential to differentiate into cells of other phenotypes. The method comprises (a) obtaining human umbilical tissue; (b) removing substantially all of blood to yield a substantially blood-free umbilical tissue, (c) dissociating the tissue by mechanical or enzymatic treatment, or both, (d) resuspending the tissue in a culture medium, and (e) providing growth conditions which allow for the growth of a human umbilicus-derived cell capable of self-renewal and expansion in culture and having the potential to differentiate into cells of other phenotypes. Tissue can be obtained from any completed pregnancy, term or less than term, whether delivered vaginally, or through other routes, for example surgical Cesarean section. Obtaining tissue from tissue banks is also considered within the scope of the present invention.

The tissue is rendered substantially free of blood by any means known in the art. For example, the blood can be physically removed by washing, rinsing, and diluting and the like, before or after bulk blood removal for example by suctioning or draining. Other means of obtaining a tissue substantially free of blood cells might include enzymatic or chemical treatment.

Dissociation of the umbilical tissues can be accomplished by any of the various techniques known in the art, including by mechanical disruption, for example, tissue can be aseptically cut with scissors, or a scalpel, or such tissue can be otherwise minced, blended, ground, or homogenized in any manner that is compatible with recovering intact or viable cells from human tissue.

In a presently preferred embodiment, the isolation procedure also utilizes an enzymatic digestion process. Many enzymes are known in the art to be useful for the isolation of individual cells from complex tissue matrices to facilitate growth in culture. As discussed above, a broad range of digestive enzymes for use in cell isolation from tissue is available to the skilled artisan. Ranging from weakly digestive (e.g. deoxyribonucleases and the neutral protease, dispase) to strongly digestive (e.g. papain and trypsin), such enzymes are available commercially. A nonexhaustive list of enzymes compatable herewith includes mucolytic enzyme activities, metalloproteases, neutral proteases, serine proteases (such as trypsin, chymotrypsin, or elastase), and deoxyribonucleases. Presently preferred are enzyme activites selected from metalloproteases, neutral proteases and mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used.

The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE BLENDZYME (Roche) series of enzyme combinations of collagenase and neutral protease are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37.degree. C. during the enzyme treatment of the dissociation step. Diluting the digest may also improve yields of cells as cells may be trapped within a viscous digest.

While the use of enzyme activites is presently preferred, it is not required for isolation methods as provided herein. Methods based on mechanical separation alone may be successful in isolating the instant cells from the umbilicus as discussed above.

The cells can be resuspended after the tissue is dissociated into any culture medium as discussed herein above. Cells may be resuspended following a centrifugation step to separate out the cells from tissue or other debris. Resuspension may involve mechanical methods of resuspending, or simply the addition of culture medium to the cells.

Providing the growth conditions allows for a wide range of options as to culture medium, supplements, atmospheric conditions, and relative humidity for the cells. A preferred temperature is 37.degree. C., however the temperature may range from about 35.degree. C. to 39.degree. C. depending on the other culture conditions and desired use of the cells or culture.

Presently preferred are methods which provide cells which require no exogenous growth factors, except as are available in the supplemental serum provided with the Growth Medium. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately resuspended and grown in. In this sense, the method is selective for those cells capable of division in the absence of the particular growth factors. Preferred cells in some embodiments are capable of growth and expansion in chemically-defined growth media with no serum added. In such cases, the cells may require certain growth factors, which can be added to the medium to support and sustain the cells.

Presently preferred factors to be added for growth on serum-free media include one or more of FGF, EGF, IGF, and PDGF. In more preferred embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Preferred are those methods which derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. Preferably these cell numbers are produced within 80, 70, or 60 days or less. In one embodiment, cord tissue mesenchymal stem cells are isolated and expanded, and possess one or more markers selected from a group comprising of CD10, CD13, CD44, CD73, CD90, CD141, PDGFr-alpha, or HLA-A, B, C. In addition, the cells do not produce one or more of CD31, CD34, CD45, CD117, CD141, or HLA-DR, DP, DQ.

In one embodiment, bone marrow MSC lots are generated, means of generating BM MSC are known in the literature and examples are incorporated by reference.

In one embodiment BM-MSC are generated as follows
1. 500 mL Isolation Buffer is prepared (PBS+2% FBS+2 mM EDTA) using sterile components or filtering Isolation Buffer through a 0.2 micron filter. Once made, the Isolation Buffer was stored at 2-8.degree. C.
2. The total number of nucleated cells in the BM sample is counted by taking 10.mu.L BM and diluting it 1/50-1/100 with 3% Acetic Acid with Methylene Blue (STEMCELL Catalog #07060). Cells are counted using a hemacytometer.
3. 50 mL Isolation Buffer is warmed to room temperature for 20 minutes prior to use and bone marrow was diluted 5/14 final dilution with room temperature Isolation Buffer (e.g. 25 mL BM was diluted with 45 mL Isolation Buffer for a total volume of 70 mL).
4. In three 50 mL conical tubes (BD Catalog #352070), 17 mL Ficoll-Paque™ PLUS (Catalog #07907/07957) is pipetted into each tube. About 23 mL of the diluted BM from step 3 was carefully layered on top of the Ficoll-Paque™ PLUS in each tube.
5. The tubes are centrifuged at room temperature (15-25.degree. C.) for 30 minutes at 300.times.g in a bench top centrifuge with the brake off.
6. The upper plasma layer is removed and discarded without disturbing the plasma: Ficoll-Paque™ PLUS interface. The mononuclear cells located at the interface layer are carefully removed and placed in a new 50 mL conical tube. Mononuclear cells are resuspended with 40 mL cold (2-8.degree. C.) Isolation Buffer and mixed gently by pipetting.
7. Cells were centrifuged at 300.times.g for 10 minutes at room temperature in a bench top centrifuge with the brake on. The supernatant is removed and the cell pellet resuspended in 1-2 mL cold Isolation Buffer.
8. Cells were diluted 1/50 in 3% Acetic Acid with Methylene Blue and the total number of nucleated cells counted using a hemacytometer.
9. Cells are diluted in Complete Human MesenCult®-Proliferation medium (STEMCELL catalog #05411) at a final concentration of $1 \times 10^6$ cells/mL.
10. BM-derived cells were ready for expansion and CFU-F assays in the presence of GW2580, which can then be used for specific applications.

Said BM-MSC are derived in lots and cells from said lots are assayed for presence of TNFR-1, ENA-78, and IGFBP-3. Lots containing higher expression of one or more proteins selected from the group of TNFR-1, ENA-78, and IGFBP-3 are chosen for utilization.

In one embodiment of the invention MSC are selected for expression of enhanced levels of one or more proteins selected from a group comprising of TNFR-1, ENA-78, and IGFBP-3.

In one embodiment, MSC are generated according to protocols previously utilized for treatment of patients utilizing bone marrow derived MSC. Specifically, bone marrow is aspirated (10-30 ml) under local anesthesia (with or without sedation) from the posterior iliac crest, collected into sodium heparin containing tubes and transferred to a Good Manufacturing Practices (GMP) clean room. Bone marrow cells are washed with a washing solution such as Dulbecco's phosphate-buffered saline (DPBS), RPMI, or PBS supplemented with autologous patient plasma and layered on to 25 ml of Percoll (1.073 g/ml) at a concentration of approximately $1-2 \cdot 10^7$ cells/ml. Subsequently the cells are centrifuged at 900 g for approximately 30 min or a time period sufficient to achieve separation of mononuclear cells from debris and erythrocytes. Said cells are then washed with PBS and plated at a density of approximately $1 \cdot 10^6$ cells per ml in 175 cm$^2$ tissue culture flasks in DMEM with 10% FCS with flasks subsequently being loaded with a minimum of 30 million bone marrow mononuclear cells. The MSCs are allowed to adhere for 72 h followed by media changes every 3-4 days. Adherent cells are removed with 0.05% trypsin-EDTA and replated at a density of $1' 10^6$ per 175 cm$^2$. Said bone marrow MSC may be administered intravenously, or in a preferred embodiment, intrathecally in a patient suffering radiation associated neurodegenerative manifestations. Although doses may be determined by one of skill in the art, and are dependent on various patient characteristics, intravenous administration may be performed at concentrations ranging from 1-10 million MSC per kilogram, with a preferred dose of approximately 2-5 million cells per kilogram.

In some embodiments of the invention MSC are transferred to possess enhanced neuromodulatory and neuroprotective properties. Said transfection may be accomplished by use of lentiviral vectors, said means to perform lentiviral mediated transfection are well-known in the art and discussed in the following references [68-74]. Some specific examples of lentiviral based transfection of genes into MSC include transfection of SDF-1 to promote stem cell homing, particularly hematopoietic stem cells [75], GDNF to treat Parkinson's in an animal model [76], HGF to accelerate remyelination in a brain injury model [77], akt to protect against pathological cardiac remodeling and cardiomyocyte death [78], TRAIL to induce apoptosis of tumor cells [79-82], PGE-1 synthase for cardioprotection [83], NUR77 to enhance migration [84], BDNF to reduce ocular nerve damage in response to hypertension [85], HIF-1 alpha to stimulate osteogenesis [86], dominant negative CCL2 to reduce lung fibrosis [87], interferon beta to reduce tumor progression [88], HLA-G to enhance immune suppressive activity [89], hTERT to induce differentiation along the hepatocyte lineage [90], cytosine deaminase [91], OCT-4 to reduce senescence [92, 93], BAMBI to reduce TGF expression and protumor effects [94], HO-1 for radioprotection [95], LIGHT to induce antitumor activity [96], miR-126 to enhance angiogenesis [97, 98], bcl-2 to induce generation of nucleus pulposus cells [99], telomerase to induce neurogenesis [100], CXCR4 to accelerate hematopoietic recovery [101] and reduce unwanted immunity [102], wnt11 to promote regenerative cytokine production [103], and the HGF antagonist NK4 to reduce cancer [104].

Cell cultures are tested for sterility weekly, endotoxin by limulus amebocyte lysate test, and *mycoplasma* by DNA-fluorochrome stain.

In order to determine the quality of MSC cultures, flow cytometry is performed on all cultures for surface expression of SH-2, SH-3, SH-4 MSC markers and lack of contaminating CD14- and CD-45 positive cells. Cells were detached with 0.05% trypsin-EDTA, washed with DPBS+2% bovine albumin, fixed in 1% paraformaldehyde, blocked in 10% serum, incubated separately with primary SH-2, SH-3 and SH-4 antibodies followed by PE-conjugated anti-mouse IgG(H+L) antibody. Confluent MSC in 175 $cm^2$ flasks are washed with Tyrode's salt solution, incubated with medium 199 (M199) for 60 min, and detached with 0.05% trypsin-EDTA (Gibco). Cells from 10 flasks were detached at a time and MSCs were resuspended in 40 ml of M199+1% human serum albumin (HSA; American Red Cross, Washington D.C., USA). MSCs harvested from each 10-flask set were stored for up to 4 h at 4° C. and combined at the end of the harvest. A total of 2-10'$10^6$ MSC/kg were resuspended in M199+1% HSA and centrifuged at 460 g for 10 min at 20° C. Cell pellets were resuspended in fresh M199+1% HSA media and centrifuged at 460 g for 10 min at 20° C. for three additional times. Total harvest time was 2-4 h based on MSC yield per flask and the target dose. Harvested MSC were cryopreserved in Cryocyte (Baxter, Deerfield, Ill., USA) freezing bags using a rate controlled freezer at a final concentration of 10% DMSO (Research Industries, Salt Lake City, Utah, USA) and 5% HSA. On the day of infusion cryopreserved units were thawed at the bedside in a 37° C. water bath and transferred into 60 ml syringes within 5 min and infused intravenously into patients over 10-15 min. Patients are premedicated with 325-650 mg acetaminophen and 12.5-25 mg of diphenhydramine orally. Blood pressure, pulse, respiratory rate, temperature and oxygen saturation are monitored at the time of infusion and every 15 min thereafter for 3 h followed by every 2 h for 6 h.

In one embodiment of the invention enhanced MSC are transfected with anti-apoptotic proteins to enhance in vivo longevity. The present invention includes a method of using MSC that have been cultured under conditions to express increased amounts of at least one anti-apoptotic protein as a therapy to inhibit or prevent apoptosis. In one embodiment, the MSC which are used as a therapy to inhibit or prevent apoptosis have been contacted with an apoptotic cell. The invention is based on the discovery that MSC that have been contacted with an apoptotic cell express high levels of anti-apoptotic molecules. In some instances, the MSC that have been contacted with an apoptotic cell secrete high levels of at least one anti-apoptotic protein, including but not limited to, STC-1, BCL-2, XIAP, Survivin, and Bcl-2XL. Methods of transfecting antiapoptotic genes into MSC have been previously described which can be applied to the current invention, said antiapoptotic genes that can be utilized for practice of the invention, in a nonlimiting way, include GATA-4 [105], FGF-2 [106], bcl-2 [99, 107], and HO-1 [108]. Based upon the disclosure provided herein, MSC can be obtained from any source. The MSC may be autologous with respect to the recipient (obtained from the same host) or allogeneic with respect to the recipient. In addition, the MSC may be xenogeneic to the recipient (obtained from an animal of a different species). In one embodiment of the invention MSC are pretreated with agents to induce expression of antiapoptotic genes, one example is pretreatment with exendin-4 as previously described [109]. In a further non-limiting embodiment, MSC used in the present invention can be isolated, from the bone marrow of any species of mammal, including but not limited to, human, mouse, rat, ape, gibbon, bovine. In a non-limiting embodiment, the MSC are isolated from a human, a mouse, or a rat. In another non-limiting embodiment, the MSC are isolated from a human.

Based upon the present disclosure, MSC can be isolated and expanded in culture in vitro to obtain sufficient numbers of cells for use in the methods described herein provided that the MSC are cultured in a manner that promotes contact with a tumor endothelial cell. For example, MSC can be isolated from human bone marrow and cultured in complete medium (DMEM low glucose containing 4 mM L-glutamine, 10% FBS, and 1% penicillin/streptomycin) in hanging drops or on non-adherent dishes. The invention, however, should in no way be construed to be limited to any one method of isolating and/or to any culturing medium. Rather, any method of isolating and any culturing medium should be construed to be included in the present invention provided that the MSC are cultured in a manner that provides MSC to express increased amounts of at least one anti-apoptotic protein. Culture conditions for growth of clinical grade MSC have been described in the literature and are incorporated by reference [110-143].

Without being limited to any one or more explanatory mechanisms for the immunomodulatory, regenerative and other properties, activities, and effects of enhanced MSC, it is worth nothing that they can modulate immune responses through a variety of modalities. For instance, enhanced MSC can have direct effects on a graft or host. Such direct effects are primarily a matter of direct contact between enhanced MSC and cells of the host or graft. The contact may be with structural members of the cells or with constituents in their immediate environment. Such direct mechanisms may involve direct contact, diffusion, uptake, or other processes well known to those skilled in the art. The direct activities and effects of the enhanced MSC may be limited spatially, such as to an area of local deposition or to a bodily compartment accessed by injection.

Enhanced MSC also can "home" in response to "homing" signals, such as those released at sites of injury or disease. Since homing often is mediated by signals whose natural function is to recruit cells to the sites where repairs are needed, the homing behavior can be a powerful tool for concentrating Enhanced MSC to therapeutic targets. This effect can be stimulated by specific factors, as discussed below.

Enhanced MSC may also modulate immune processes by their response to factors. This may occur additionally or alternatively to direct modulation. Such factors may include homing factors, mitogens, and other stimulatory factors. They may also include differentiation factors, and factors that trigger particular cellular processes. Among the latter are factors that cause the secretion by cells of other specific factors, such as those that are involved in recruiting cells, such as stem cells (including Enhanced MSC), to a site of injury or disease.

Enhanced MSC may, in addition to the foregoing or alternatively thereto, secrete factors that act on endogenous cells, such as stem cells or progenitor cells. The factors may act on other cells to engender, enhance, decrease, or suppress their activities. eEhanced MSC may secrete factors that act on stem, progenitor, or differentiated cells causing those cells to divide and/or differentiate. One such factor is exosomes and microvesicles produced by said enhanced MSC. Enhanced MSC that home to a site where repair is needed may secrete trophic factors that attract other cells to the site. In this way, Enhanced MSC may attract stem, progenitor, or differentiated cells to a site where they are needed. Enhanced MSC also may secrete factors that cause such cells to divide or differentiate. Secretion of such factors, including trophic factors, can contribute to the efficacy of enhanced MSC in, for instance, limiting inflammatory damage, limiting vascular permeability, improving cell survival, and engendering and/or augmenting homing of repair cells to sites of damage. Such factors also may affect T-cell proliferation directly. Such factors also may affect dendritic cells, by decreasing their phagocytic and antigen presenting activities, which also may affect T-cell activity. Furthermore such factors, or Enhanced MSC themselves, may be capable of modulating T regulatory cell numbers.

By these and other mechanisms, enhanced MSC can provide beneficial immunomodulatory effects, including, but not limited to, suppression of undesirable and/or deleterious immune reactions, responses, functions, diseases, and the like. Enhanced MSC in various embodiments of the invention provide beneficial immunomodulatory properties and effects that are useful by themselves or in adjunctive therapy for precluding, preventing, lessening, decreasing, ameliorating, mitigating, treating, eliminating and/or curing deleterious immune processes and/or conditions. Such processes and conditions include, for instance, autoimmune diseases, anemias, neoplasms, HVG, GVHD, and certain inflammatory disorders. In one particular embodiment, said enhanced MSC are useful for treatment of Neurological disease, inflammatory conditions, psychiatric disorders, inborn errors of metabolisms, vascular disease, cardiac disease, renal disease, hepatic disease, pulmonary disease, ocular conditions such as uveitis, gastrointestinal disorders, orthopedic disorders, dermal disorders, neoplasias, prevention of neoplasias, hematopoietic disorders, reproductive disorders, gynecological disorders, urological disorders, immunological disorders, olfactory disorders, and auricular disorders.

Enhanced MSC are useful in these other regards particularly in mammals. In various embodiments of the invention in this regard, Enhanced MSC are used therapeutically in human patients, often adjunctively to other therapies.

In one embodiment, enhanced MSC are utilized as a source of exosomes for inhibition of autoimmunity, or more specifically for treatment of RA. Exosomes may be purified based on expression of various markers. Said markers may comprise one or more tetraspanins, typically CD63, CD81, CD9, CD53, CD82 and/or CD37, which are disclosed in various publications, exemplary ones incorporated herein by reference [144-146]. Expression of exosome surface markers may be determined, for example, by means of flow cytometry and/or FACS for a specific cell surface marker using conventional methods and apparatus (for example a Beckman Coulter Epics XL FACS system used with commercially available antibodies and standard protocols known in the art) to determine whether the signal for a specific microparticle surface marker is greater than a background signal. The background signal is defined as the signal intensity generated by a non-specific antibody of the same isotype as the specific antibody used to detect each surface marker. For a marker to be considered positive the specific signal observed is typically more than 20%, preferably stronger than 30%, 40%, 50%, 60%, 70%, 80%, 90%, 100%, 500%, 1000%, 5000%, 10000% or above, greater relative to the background signal intensity. Alternative methods for analysing expression of microparticle surface markers of interest include visual analysis by electron microscopy using antibodies against cell-surface markers of interest. "Fluorescence activated cell sorting (FACS)" is a method of cell purification based on the use of fluorescent labelled antibodies. The antibodies are directed to a marker on the cell surface, and therefore bind to the cells of interest. The cells are then separated based upon the fluorescent emission peak of the cells. Furthermore, exosome and/or microparticle markers (including surface and intracellular proteins) can also be analysed by various methods known to one skilled in the art to assay protein expression, including but not limited to gel electrophoresis followed by western blotting with suitable antibodies, immunoprecipitation followed by electrophoretic analysis, and/or electron microscopy as described above, with microparticle permeabilisation for intraparticle markers. For example, expression of one or more tetraspanins may be assayed using one or more of the above methods or any other method known to one skilled in the art. RNA levels may also be analysed to assess marker expression, for example qRT-PCR.

Within the context of the invention, exosomes and microparticles may be used interchangeably. Exosomes from enhanced MSC may be generated from a mesenchymal stem cell conditioned medium (MSC-CM). Said particle may be isolated for example by being separated from non-associated components based on any property of the particle. For example, the particle may be isolated based on molecular weight, size, shape, composition or biological activity. The conditioned medium may be filtered or concentrated or both during, prior to or subsequent to separation. For example, it may be filtered through a membrane, for example one with a size or molecular weight cut-off. It may be subject to tangential force filtration or ultrafiltration. Filtration of conditioned media is described in the following and incorporated by reference [147]. For example, filtration with a membrane of a suitable molecular weight or size cutoff. The conditioned medium, optionally filtered or concentrated or both, may be subject to further separation means, such as column chromatography. For example, high performance liquid chromatography (HPLC) with various columns may be used. The columns may be size exclusion columns or binding columns. One or more properties or biological activities of the particle may be used to track its activity during fractionation of the mesenchymal stem cell conditioned medium (MSC-CM). As an example, light scattering, refractive index, dynamic light scattering or UV-visible detectors may be used to follow the particles. For example, a therapeutic activity such as antirheumatic activity may be used to track the activity during fractionation. In one embodiment antirheumatic activity is assessed by ability to inhibit TNF-alpha production from stimulated monocytes or monocytic lineage cell such as macrophages or dendritic cells.

In one aspect of the invention enhanced MSC are cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6.times.40 mm or a TSK gel G4000 SWXL, 7.8.times.300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of particles in this peak is about 45-55 nm. Such fractions comprise mesenchymal stem cell particles such as exosomes.

Enhanced MSC can be prepared from a variety of tissues, such as bone marrow cells [148-154], umbilical cord tissue [155-157], peripheral blood [158-160], amniotic membrane [161], amniotic fluid, mobilized peripheral blood [162], adipose tissue [163, 164], endometrium and other tissues. When tissue sources of MSC are used said tissue isolates from which the Enhanced MSC are isolated comprise a mixed populations of cells. Enhanced MSC constitute a very small percentage in these initial populations. They must be purified away from the other cells before they can be expanded in culture sufficiently to obtain enough cells for therapeutic applications.

In some embodiments the enhanced MSC preparations are clonally derived. In principle, the Enhanced MSC in these preparations are genetically identical to one another and, if properly prepared and maintained, are free of other cells. In some embodiments enhanced MSC preparations that are less pure than these may be used. While rare, less pure populations may arise when the initial cloning step requires more than one cell. If these are not all enhanced MSC, expansion will produce a mixed population in which enhanced MSC are only one of at least two types of cells. More often mixed populations arise when enhanced MSC are administered in admixture with one or more other types of cells.

In many embodiments the purity of enhanced MSC for administration to a subject is about 100%. In other embodiments it is 95% to 100%. In some embodiments it is 85% to 95%. Particularly in the case of admixtures with other cells, the percentage of Enhanced MSC can be 25%-30%, 30%-35%, 35%-40%, 40%-45%, 45%-50%, 60%-70%, 70%-80%, 80%-90%, or 90%-95%.

In some embodiments enhanced MSC possess a superior ability to modulate pro-autoimmune activities of macrophages, assessed as previously described in the following, which is incorporated by reference [165].

The number of enhanced MSC in a given volume can be determined by well known and routine procedures and instrumentation. The percentage of enhanced MSC in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

Enhanced MSC immunomodulation may involve undifferentiated enhanced MSC. It may involve enhnaced MSC that are committed to a differentiation pathway. Such immunomodulation also may involve enhanced MSC that have differentiated into a less potent stem cell with limited differentiation potential. It also may involve enhanced MSC that have differentiated into a terminally differentiated cell type. The best type or mixture of enhanced MSC will be determined by the particular circumstances of their use, and it will be a matter of routine design for those skilled in the art to determine an effective type or combination of enhanced MSC.

The choice of formulation for administering enhanced MSC for a given application will depend on a variety of factors. Prominent among these will be the species of subject, the nature of the disorder, dysfunction, or disease being treated and its state and distribution in the subject, the nature of other therapies and agents that are being administered, the optimum route for administration of the enhanced MSC, survivability of enhanced MSC via the route, the dosing regimen, and other factors that will be apparent to those skilled in the art. In particular, for instance, the choice of suitable carriers and other additives will depend on the exact route of administration and the nature of the particular dosage form, for example, liquid dosage form (e.g., whether the composition is to be formulated into a solution, a suspension, gel or another liquid form, such as a time release form or liquid-filled form).

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic Enhanced MSC. Various embodiments of the invention comprise measures to increase cell survival and/or to overcome problems posed by barriers to seeding and/or growth.

Examples of compositions comprising enhanced MSC include liquid preparations, including suspensions and preparations for intramuscular or intravenous administration (e.g., injectable administration), such as sterile suspensions or emulsions. Such compositions may comprise an admixture of Enhanced MSC with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention often are conveniently provided as liquid preparations, e.g., isotonic aqueous solutions, suspensions, emulsions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Various additives often will be included to enhance the stability, sterility, and isotonicity of the compositions, such as antimicrobial preservatives, antioxidants, chelating agents, and buffers, among others. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents that delay absorption, for example, aluminum monostearate, and gelatin. According to the present invention, however, any vehicle, diluent, or additive used would have to be compatible with the cells.

Enhanced MSC solutions, suspensions, and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose) may also be present.

Typically, the compositions will be isotonic, i.e., they will have the same osmotic pressure as blood and lacrimal fluid when properly prepared for administration.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of enhanced MSC compositions. If such preservatives are included, it is well within the purview of the skilled artisan to select compositions that will not affect the viability or efficacy of the enhanced MSC.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

In some embodiments, enhanced MSC are formulated in a unit dosage injectable form, such as a solution, suspension, or emulsion. Pharmaceutical formulations suitable for injection of Enhanced MSC typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

For any composition to be administered to an animal or human, and for any particular method of administration, it is preferred to determine therefore: toxicity, such as by determining the lethal dose (LD) and LD50 in a suitable animal model, e.g., rodent such as mouse or rat; and, the dosage of the composition(s), concentration of components therein, and timing of administering the composition(s), which elicit a suitable response. Such determinations do not require undue experimentation from the knowledge of the skilled artisan, this disclosure, and the documents cited herein. And, the time for sequential administrations can be ascertained without undue experimentation.

In some embodiments Enhanced MSC are encapsulated for administration, particularly where encapsulation enhances the effectiveness of the therapy, or provides advantages in handling and/or shelf life. Encapsulation in some embodiments where it increases the efficacy of ENHANCED MSC mediated immunosuppression may, as a result, also reduce the need for immunosuppressive drug therapy.

Also, encapsulation in some embodiments provides a barrier to a subject's immune system that may further reduce a subject's immune response to the Enhanced MSC (which generally are not immunogenic or are only weakly immunogenic in allogeneic transplants), thereby reducing any graft rejection or inflammation that might occur upon administration of the cells.

In a variety of embodiments where enhanced MSC are administered in admixture with cells of another type, which are more typically immunogenic in an allogeneic or xenogeneic setting, encapsulation may reduce or eliminate adverse host immune responses to the non-enhanced MSC cells and/or GVHD that might occur in an immunocompromised host if the admixed cells are immunocompetent and recognize the host as non-self.

Enhanced MSC may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of Enhanced MSC. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of Enhanced MSC are known to those of skill in the art and are described, for example, in Chang, P., et al., 1999; Matthew, H. W., et al., 1991; Yanagi, K., et al., 1989; Cal Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of Enhanced MSC.

Certain embodiments incorporate Enhanced MSC into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, Enhanced MSC may be incorporated in the interstices of a three-dimensional gel. A large polymer or gel, typically, will be surgically implanted. A polymer or gel that can be formulated in small enough particles or fibers can be administered by other common, more convenient, non-surgical routes.

Pharmaceutical compositions of the invention may be prepared in many forms that include tablets, hard or soft gelatin capsules, aqueous solutions, suspensions, and liposomes and other slow-release formulations, such as shaped polymeric gels. Oral liquid pharmaceutical compositions may be in the form of, for example, aqueous or oily suspensions, solutions, emulsions, syrups, or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives. An oral dosage form may be formulated such that cells are released into the intestine after passing through the stomach. Such formulations are described in U.S. Pat. No. 6,306,434 and in the references contained therein.

Pharmaceutical compositions suitable for rectal administration can be prepared as unit dose suppositories. Suitable carriers include saline solution and other materials commonly used in the art.

For administration by inhalation, cells can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, a means may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, cells may be administered via a liquid spray, such as via a plastic bottle atomizer.

Enhanced MSC may be administered with other pharmaceutically active agents. In some embodiments one or more of such agents are formulated together with Enhanced MSC for administration. In some embodiments the Enhanced MSC and the one or more agents are in separate formulations. In some embodiments the compositions comprising the Enhanced MSC and/or the one or more agents are formulated with regard to adjunctive use with one another.

Enhanced MSC may be administered in a formulation comprising a immunosuppressive agents, such as any combination of any number of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506 and rapamycin. In certain embodiments, such agents include a corticosteroid, cyclosporin A, azathioprine, cyclophosphamide, rapamycin, and/or FK-506. Immunosuppressive agents in accordance with the foregoing may be the only such additional agents or may be combined with other agents, such as other agents noted herein. Other immunosuppressive agents include Tacrolimus, Mycophenolate mofetil, and Sirolimus.

Such agents also include antibiotic agents, antifungal agents, and antiviral agents, to name just a few other pharmacologically active substances and compositions that may be used in accordance with embodiments of the invention.

Typical antibiotics or anti-mycotic compounds include, but are not limited to, penicillin, streptomycin, amphotericin, ampicillin, gentamicin, kanamycin, mycophenolic acid, nalidixic acid, neomycin, nystatin, paromomycin, polymyxin, puromycin, rifampicin, spectinomycin, tetracycline, tylosin, zeocin, and cephalosporins, aminoglycosides, and echinocandins.

Further additives of this type relate to the fact that Enhanced MSC, like other stems cells, following administration to a subject may "home" to an environment favorable to their growth and function. Such "homing" often concentrates the cells at sites where they are needed, such as sites of immune disorder, dysfunction, or disease. A number of substances are known to stimulate homing. They include growth factors and trophic signaling agents, such as cytokines. They may be used to promote homing of Enhanced MSC to therapeutically targeted sites. They may be administered to a subject prior to treatment with Enhanced MSC, together with enhanced MSC, or after enhanced MSC are administered.

Certain cytokines, for instance, alter or affect the migration of enhanced MSC or their differentiated counterparts to sites in need of therapy, such as immunocompromised sites. Cytokines that may be used in this regard include, but are not limited to, stromal cell derived factor-1 (SDF-1), stem cell factor (SCF), angiopoietin-1, placenta-derived growth factor (PlGF), granulocyte-colony stimulating factor (G-CSF), cytokines that stimulate expression of endothelial adhesion molecules such as ICAMs and VCAMs, and cytokines that engender or facilitate homing.

They may be administered to a subject as a pre-treatment, along with Enhanced MSC, or after enhanced MSC have been administered, to promote homing to desired sites and to achieve improved therapeutic effect, either by improved homing or by other mechanisms. Such factors may be combined with Enhanced MSC in a formulation suitable for them to be administered together. Alternatively, such factors may be formulated and administered separately.

Order of administration, formulations, doses, frequency of dosing, and routes of administration of factors (such as the cytokines discussed above) and Enhanced MSC generally will vary with the disorder or disease being treated, its severity, the subject, other therapies that are being administered, the stage of the disorder or disease, and prognostic factors, among others. General regimens that have been established for other treatments provide a framework for determining appropriate dosing in enhanced MSC-mediated direct or adjunctive therapy. These, together with the additional information provided herein, will enable the skilled artisan to determine appropriate administration procedures in accordance with embodiments of the invention, without undue experimentation.

Enhanced MSC can be administered to a subject by any of a variety of routes known to those skilled in the art that may be used to administer cells to a subject.

Among methods that may be used in this regard in embodiments of the invention are methods for administering enhanced MSC by a parenteral route. Parenteral routes of administration useful in various embodiments of the invention include, among others, administration by intravenous, intraarterial, intracardiac, intraspinal, intrathecal, intraosseous, intraarticular, intrasynovial, intracutaneous, intradermal, subcutaneous, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

In various embodiments of the invention enhanced MSC are administered by systemic injection. Systemic injection, such as intravenous injection, offers one of the simplest and least invasive routes for administering enhanced MSC. In some cases, these routes may require high enhanced MSC doses for optimal effectiveness and/or homing by the enhanced MSC to the target sites. In a variety of embodiments enhanced MSC may be administered by targeted and/or localized injections to ensure optimum effect at the target sites.

Enhanced MSC may be administered to the subject through a hypodermic needle by a syringe in some embodiments of the invention. In various embodiments, enhanced MSC are administered to the subject through a catheter. In a variety of embodiments, enhanced MSC are administered by surgical implantation. Further in this regard, in various embodiments of the invention, Enhanced MSC are administered to the subject by implantation using an arthroscopic procedure. In some embodiments Enhanced MSC are administered to the subject in or on a solid support, such as a polymer or gel. In various embodiments, Enhanced MSC are administered to the subject in an encapsulated form.

In additional embodiments of the invention, Enhanced MSC are suitably formulated for oral, rectal, epicutaneous, ocular, nasal, and/or pulmonary delivery and are administered accordingly.

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of enhanced MSC appropriate to be used in accordance with various embodiments of the invention will depend on numerous factors. It may vary considerably for different circumstances. The parameters that will determine optimal doses of enhanced MSC to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the Enhanced MSC are syngeneic, autologous, allogeneic, or xenogeneic; their potency (specific activity); the site and/or distribution that must be targeted for the Enhanced MSC to be effective; and such characteristics of the site such as accessibility to Enhanced MSC and/or engraftment of Enhanced MSC. Additional parameters include co-administration with Enhanced MSC of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of Enhanced MSC outweighs the advantages of the increased dose.

The optimal dose of enhanced MSC for some embodiments will be in the range of doses used for autologous, mononuclear bone marrow transplantation. For fairly pure preparations of enhanced MSC, optimal doses in various embodiments will range from $10^4$ to $10^8$ enhanced MSC cells/kg of recipient mass per administration. In some embodiments the optimal dose per administration will be between $10^5$ to $10^7$ enhanced MSC cells/kg. In many embodiments the optimal dose per administration will be $5 \times 10^5$ to $5 \times 10^6$ enhanced MSC cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, Enhanced MSC may be administered in an initial dose, and thereafter maintained by further administration of Enhanced MSC. Enhanced MSC may be administered by one method initially, and thereafter administered by the same method or one or more different methods. The subject's MSC levels can be maintained by the ongoing administration of the cells. Various embodiments administer the Enhanced MSC either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regiments can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer Enhanced MSC.

In some embodiments Enhanced MSC are administered to a subject in one dose. In others Enhanced MSC are administered to a subject in a series of two or more doses in succession. In some other embodiments wherein Enhanced MSC are administered in a single dose, in two doses, and/or more than two doses, the doses may be the same or different, and they are administered with equal or with unequal intervals between them.

Enhanced MSC may be administered in many frequencies over a wide range of times. In some embodiments, enhanced MSC are administered over a period of less than one day. In other embodiment they are administered over two, three, four, five, or six days. In some embodiments Enhanced MSC are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

The immunomodulatory properties of enhanced MSC may be used in treating a wide variety of disorders, dysfunctions and diseases, such as those that, intrinsically, as a secondary effect or as a side effect of treatment, present with deleterious immune system processes and effects. Several illustrations are discussed below.

In a variety of embodiments involving transplant therapies, enhanced MSC can be used alone for an immunosuppressive purpose, or together with other agents. Enhanced MSC can be administered before, during, or after one or more transplants. If administered during transplant, enhanced MSC can be administered separately or together with transplant material. If separately administered, the Enhanced MSC can be administered sequentially or simultaneously with the other transplant materials. Furthermore, Enhanced MSC may be administered well in advance of the transplant and/or well after, alternatively to or in addition to administration at or about the same time as administration of the transplant.

Other agents that can be used in conjunction with enhanced MSC, in transplantation therapies in particular, include immunomodulatory agents, such as those described elsewhere herein, particularly immunosuppressive agents, more particularly those described elsewhere herein, especially in this regard, one or more of a corticosteroid, cyclosporin A, a cyclosporin-like immunosuppressive compound, azathioprine, cyclophosphamide, methotrexate, and an immunosuppressive monoclonal antibody agent.

Enhanced MSC can modulate immune responses. In particular in this regard, it has been found that Enhanced MSC can suppress immune responses, including but not limited to immune responses involved in, for example, HVG response and GVHD, to name just two. In an even more detailed particular in this regard, it has been found that Enhanced MSC can suppress proliferation of T-cells, even in the presence of potent T-cell stimulators, such as Concanavalin A and allogeneic or xenogeneic stimulator cells.

Moreover, it has been found that even relatively small amounts of enhanced MSC can suppress these responses. Indeed, only 3% Enhanced MSC in mixed lymphocyte reactions is sufficient to reduce T-cell response by 50% in vitro.

Embodiments of the invention relate to using enhanced MSC immunomodulation to treat an immune dysfunction, disorder, or disease, either solely, or as an adjunctive therapy. Embodiments in this regard relate to congenital immune deficiencies and autoimmune dysfunctions, disorders, and diseases. Various embodiments relate, in this regard, to using Enhanced MSC to treat, solely or adjunctively, Crohn's disease, Guillain-Barre syndrome, lupus erythematosus (also called "SLE" and systemic lupus erythematosus), multiple sclerosis, myasthenia gravis, optic neuritis, psoriasis, rheumatoid arthritis, Graves' disease, Hashimoto's disease, Ord's thyroiditis, diabetes mellitus (type 1), Reiter's syndrome, autoimmune hepatitis, primary biliary cirrhosis, antiphospholipid antibody syndrome ("APS"), opsoclonus-myoclonus syndrome ("OMS"), temporal arteritis, acute disseminated encephalomyelitis ("ADEM" and "ADE"), Goodpasture's, syndrome, Wegener's granulomatosis, celiac disease, pemphigus, polyarthritis, autism, autism spectrum disorder, post traumatic stress disorder, and warm autoimmune hemolytic anemia.

Particular embodiments among these relate to Crohn's disease, lupus erythematosus (also called "SLE" and systemic lupus erythematosus), multiple sclerosis, myasthenia gravis, psoriasis, rheumatoid arthritis, Graves' disease, Hashimoto's disease, diabetes mellitus (type 1), Reiter's syndrome, primary biliary cirrhosis, celiac disease, polyarhritis, and warm autoimmune hemolytic anemia.

In addition, enhanced MSC are used in a variety of embodiments in this regard, solely and, typically, adjunctively, to treat a variety of diseases thought to have an autoimmune component, including but not limited to embodiments that may be used to treat endometriosis, interstitial cystitis, neuromyotonia, scleroderma, progressive systemic scleroderma, vitiligo, vulvodynia, Chagas' disease, sarcoidosis, chronic fatigue syndrome, and dysautonomia.

In one embodiment higher expression of one or more proteins selected from a group comprising of TNFR-1, ENA-78, and IGFBP-3 is utilized to select MSC generated from MSC progenitors and/or pluripotent cells Inherited immune system disorders include Severe Combined Immunodeficiency (SCID) including but not limited to SCID with Adenosine Deaminase Deficiency (ADA-SCID), SCID which is X-linked, SCID with absence of T & B Cells, SCID with absence of T Cells, Normal B Cells, Omenn Syndrome, Neutropenias including but not limited to Kostmann Syndrome, Myelokathexis; Ataxia-Telangiectasia, Bare Lymphocyte Syndrome, Common Variable Immunodeficiency, DiGeorge Syndrome, Leukocyte Adhesion Deficiency; and phagocyte Disorders (phagocytes are immune system cells that can engulf and kill foreign organisms) including but not limited to Chediak-Higashi Syndrome, Chronic Granulomatous Disease, Neutrophil Actin Deficiency, Reticular Dysgenesis. Enhanced MSC may be administered adjunctively to a treatment for any of the foregoing diseases.

In one embodiment tissue culture supernatant is derived from cultures of enhanced MSC and utilized for therapeutic applications. Use of tissue culture supernatant is described in the following patents and incorporated by reference U.S. Pat. Nos. 8,703,710; 9,192,632; 6,642,048; 7,790,455; 9,192,632; and the following patent applications; 20160022738; 20160000699; 20150024483; 20130251670;

20120294949; 20120276215; 20120195969; 20110293583; 20110171182; 20110129447; 20100159588; 20080241112.

Example 1

Extraordinary clinical results in rheumatoid arthritis patients receiving MSCs were noticed. An analysis of the cells used in treatment of patients yielded data showing that the extraordinary results were among individuals who had received a limited number of lots of MSCs. A group of four of those lots (Enhanced MSCs) was compiled and compared to a group of six lots of cells that had been used with less clinical effect (Normal MSCs) and two groups were compared in an experiment that was designed to determine if there were differences in the proteins of the supernatant from each group.

Cellular supernatants from tissue culture were evaluated with the Quantibody array by Ray Biotech, as per manufacturer's instructions. Results are presented below.

| Quantitative proteomics of supernatant of cells--Quantibody array Ray Biotech | | | | |
|---|---|---|---|---|
| | n = Enhanced MSC | n = 6 Normal MSC | P value | Percentage |
| 1TNF RI | 31.32715773 | 20.38869506 | 0.010996117 | 153.6496457 |
| 2ENA-78 | 63.23304404 | 16.31059022 | 0.020195118 | 387.6809067 |
| 3IGFBP-3 | 109.6420083 | 46.49607025 | 0.038496397 | 235.8091936 |

REFERENCES

1. Adams, N. M., et al., *NK Cell Responses Redefine Immunological Memory.* J Immunol, 2016. 197(8): p. 2963-2970.
2. Serre, L., N. Fazilleau, and S. Guerder, *Central tolerance spares the private high-avidity CD4(+) T-cell repertoire specific for an islet antigen in NOD mice.* Eur J Immunol, 2015. 45(7): p. 1946-56.
3. Enouz, S., et al., *Autoreactive T cells bypass negative selection and respond to self-antigen stimulation during infection.* J Exp Med, 2012. 209(10): p. 1769-79.
4. FIRESTEIN, G. E. a. P. o. R. A. I. H. R., Edward D., M. C. F. Genovese, Gary S.; Sargent, John S.; Sledge, Clement B., editors. Kelley's, and P. Textbook of Rheumatology. Vol. 7. Philadelphia, USA: Elsevier Saunders; 2005. p. 996-1042.
5. Sun, S., et al., *TLR7/9 antagonists as therapeutics for immune-mediated inflammatory disorders.* Inflamm Allergy Drug Targets, 2007. 6(4): p. 223-35.
6. Chong, A. S., et al., *In vivo activity of leflunomide: pharmacokinetic analyses and mechanism of immunosuppression.* Transplantation, 1999. 68(1): p. 100-9.
7. Dimitrova, P., et al., *Restriction of de novo pyrimidine biosynthesis inhibits Th1 cell activation and promotes Th2 cell differentiation.* J Immunol, 2002. 169(6): p. 3392-9.
8. Kirsch, B. M., et al., *The active metabolite of leflunomide, A771726, interferes with dendritic cell function.* Arthritis Res Ther, 2005. 7(3): p. R694-703.
9. Tepperman, K., et al., *Dicyanogold effects on lymphokine production.* Met Based Drugs, 1999. 6(4-5): p. 301-9.
10. Han, S., et al., *Auranofin, an immunosuppressive drug, inhibits MHC class I and MHC class II pathways of antigen presentation in dendritic cells.* Arch Pharm Res, 2008. 31(3): p. 370-6.
11. Kim, T. S., et al., *Inhibition of interleukin-12 production by auranofin, an anti-rheumatic gold compound, deviates CD4(+) T cells from the Th1 to the Th2 pathway.* Br J Pharmacol, 2001. 134(3): p. 571-8.
12. Taggart, A. J., *Sulphasalazine in arthritis—an old drug rediscovered.* Clin Rheumatol, 1987. 6(3): p. 378-83.
13. Bansard, C., et al., *Can rheumatoid arthritis responsiveness to methotrexate and biologics be predicted?* Rheumatology (Oxford), 2009. 48(9): p. 1021-8.
14. Bijlsma, J. W., et al., *Are glucocorticoids DMARDs?* Ann N Y Acad Sci, 2006. 1069: p. 268-74.
15. Nanda, S. and J. M. Bathon, *Etanercept: a clinical review of current and emerging indications.* Expert Opin Pharmacother, 2004. 5(5): p. 1175-86.
16. Shakoor, N., et al., *Drug-induced systemic lupus erythematosus associated with etanercept therapy.* Lancet, 2002. 359(9306): p. 579-80.
17. Dinarello, C. A., *Anti-cytokine therapeutics and infections.* Vaccine, 2003. 21 Suppl 2: p. S24-34.
18. Trentham, D. E., A. S. Townes, and A. H. Kang, *Autoimmunity to type II collagen an experimental model of arthritis.* J Exp Med, 1977. 146(3): p. 857-68.
19. Trentham, D. E., R. A. Dynesius, and J. R. David, *Passive transfer by cells of type II collagen-induced arthritis in rats.* J Clin Invest, 1978. 62(2): p. 359-66.
20. Londei, M., et al., *Persistence of collagen type II-specific T-cell clones in the synovial membrane of a patient with rheumatoid arthritis.* Proc Natl Acad Sci USA, 1989. 86(2): p. 636-40.
21. Sekine, T., et al., *Type II collagen is a target antigen of clonally expanded T cells in the synovium of patients with rheumatoid arthritis.* Ann Rheum Dis, 1999. 58(7): p. 446-50.
22. Trentham, D. E., et al., *Effects of oral administration of type II collagen on rheumatoid arthritis.* Science, 1993. 261(5129): p. 1727-30.
23. http://www.autoimmuneinc.com/clinic/coll.html.
24. Min, W. P., et al., *Synergistic tolerance induced by LF15-0195 and anti-CD45RB monoclonal antibody through suppressive dendritic cells.* Transplantation, 2003. 75(8): p. 1160-5.
25. Min, W. P., et al., *Inhibitory feedback loop between tolerogenic dendritic cells and regularoty T cells in transplant tolerance.* J Immunol, 2003. 170: p. 1304-1312.
26. Yang, J., et al., *LF15-0195 generates tolerogenic dendritic cells by suppression of NF-kappaB signaling through inhibition of IKK activity.* J Leukoc Biol, 2003. 74(3): p. 438-47.
27. Min, W. P., et al., *Dendritic cells genetically engineered to express Fas ligand induce donor-specific hyporesponsiveness and prolong allograft survival.* J Immunol, 2000. 164(1): p. 161-7.
28. Gainer, A. L., et al., *Improved survival of biolistically transfected mouse islet allografts expressing CTLA4-Ig or soluble Fas ligand.* Transplantation, 1998. 66(2): p. 194-9.
29. Ichim, T. E., et al., *RNA interference: a potent tool for gene-specific therapeutics.* Am J Transplant, 2004. 4(8): p. 1227-36.
30. Ichim, T. E., R. Zhong, and W. P. Min, *Prevention of allograft rejection by in vitro generated tolerogenic dendritic cells.* Transpl Immunol, 2003. 11(3-4): p. 295-306.
31. Hill, J. A., et al., *Immune modulation by silencing IL-12 production in dendritic cells using small interfering RNA.* J Immunol, 2003. 171(2): p. 691-6.
32. Li, M., et al., *Induction of RNA interference in dendritic cells.* Immunol Res, 2004. 30(2): p. 215-30.

33. Nasef, A., et al., *Selected Stro-1-enriched bone marrow stromal cells display a major suppressive effect on lymphocyte proliferation*. Int J Lab Hematol, 2009. 31(1): p. 9-19.
34. Nasef, A., et al., *Leukemia inhibitory factor: Role in human mesenchymal stem cells mediated immunosuppression*. Cell Immunol, 2008. 253(1-2): p. 16-22.
35. Lepelletier, Y., et al., *Galectin-1 and Semaphorin-3A are two soluble factors conferring T cell immunosuppression to bone marrow mesenchymal stem cell*. Stem Cells Dev, 2009.
36. Renner, P., et al., *Mesenchymal stem cells require a sufficient, ongoing immune response to exert their immunosuppressive function*. Transplant Proc, 2009. 41(6): p. 2607-11.
37. Ryan, J. M., et al., *Interferon-gamma does not break, but promotes the immunosuppressive capacity of adult human mesenchymal stem cells*. Clin Exp Immunol, 2007. 149(2): p. 353-63.
38. Lisheng, W., E. Meng, and Z. Guo, *High mobility group box 1 protein inhibits the proliferation of human mesenchymal stem cells and promotes their migration and differentiation along osteoblastic pathway*. Stem Cells Dev, 2008.
39. Kitaori, T., et al., *Stromal cell-derived factor 1/CXCR4 signaling is critical for the recruitment of mesenchymal stem cells to the fracture site during skeletal repair in a mouse model*. Arthritis Rheum, 2009. 60(3): p. 813-23.
40. Wang, Y., Y. Deng, and G. Q. Zhou, *SDF-1alpha/CXCR4-mediated migration of systemically transplanted bone marrow stromal cells towards ischemic brain lesion in a rat model*. Brain Res, 2008. 1195: p. 104-12.
41. Shi, M., et al., *Regulation of CXCR4 expression in human mesenchymal stem cells by cytokine treatment: role in homing efficiency in NOD/SCID mice*. Haematologica, 2007. 92(7): p. 897-904.
42. Gunzberg, W. H. and B. Salmons, *Stem cell therapies: on track but suffer setback*. Curr Opin Mol Ther, 2009. 11(4): p. 360-3.
43. Kebriaei, P., et al., *Adult human mesenchymal stem cells added to corticosteroid therapy for the treatment of acute graft-versus-host disease*. Biol Blood Marrow Transplant, 2009. 15(7): p. 804-11.
44. Dryden, G. W., *Overview of stem cell therapy for Crohn's disease*. Expert Opin Biol Ther, 2009. 9(7): p. 841-7.
45. Richardson, S. M., et al., *Mesenchymal stem cells in regenerative medicine: opportunities and challenges for articular cartilage and intervertebral disc tissue engineering*. J Cell Physiol. 222(1): p. 23-32.
46. Bouffi, C., et al., *Multipotent mesenchymal stromal cells and rheumatoid arthritis: risk or benefit?* Rheumatology (Oxford), 2009. 48(10): p. 1185-9.
47. Djouad, F., et al., *Reversal of the immunosuppressive properties of mesenchymal stem cells by tumor necrosis factor alpha in collagen-induced arthritis*. Arthritis Rheum, 2005. 52(5): p. 1595-603.
48. Mao, F., et al., *Immunosuppressive effects of mesenchymal stem cells in collagen-induced mouse arthritis*. Inflamm Res, 2009.
49. Gonzalez, M. A., et al., *Treatment of experimental arthritis by inducing immune tolerance with human adipose-derived mesenchymal stem cells*. Arthritis Rheum, 2009. 60(4): p. 1006-19.
50. Zheng, Z. H., et al., *Allogeneic mesenchymal stem cell and mesenchymal stem cell-differentiated chondrocyte suppress the responses of type II collagen-reactive T cells in rheumatoid arthritis*. Rheumatology (Oxford), 2008. 47(1): p. 22-30.
51. Karussis, D. and I. Kassis, *The potential use of stem cells in multiple sclerosis: an overview of the preclinical experience*. Clin Neurol Neurosurg, 2008. 110(9): p. 889-96.
52. Zappia, E., et al., *Mesenchymal stem cells ameliorate experimental autoimmune encephalomyelitis inducing T-cell anergy*. Blood, 2005. 106(5): p. 1755-61.
53. Casiraghi, F., et al., *Pretransplant infusion of mesenchymal stem cells prolongs the survival of a semiallogeneic heart transplant through the generation of regulatory T cells*. J Immunol, 2008. 181(6): p. 3933-46.
54. Boumaza, I., et al., *Autologous bone marrow-derived rat mesenchymal stem cells promote PDX-1 and insulin expression in the islets, alter T cell cytokine pattern and preserve regulatory T cells in the periphery and induce sustained normoglycemia*. J Autoimmun, 2008.
55. Zhou, K., et al., *Transplantation of human bone marrow mesenchymal stem cell ameliorates the autoimmune pathogenesis in MRL/lpr mice*. Cell Mol Immunol, 2008. 5(6): p. 417-24.
56. Parekkadan, B., A. W. Tilles, and M. L. Yarmush, *Bone marrow-derived mesenchymal stem cells ameliorate autoimmune enteropathy independently of regulatory T cells*. Stem Cells, 2008. 26(7): p. 1913-9.
57. Liang, J., et al., *Allogeneic mesenchymal stem cells transplantation in patients with refractory RA*. Clin Rheumatol, 2012. 31(1): p. 157-61.
58. Wang, L., et al., *Human umbilical cord mesenchymal stem cell therapy for patients with active rheumatoid arthritis: safety and efficacy*. Stem Cells Dev, 2013. 22(24): p. 3192-202.
59. Wang, L., et al., *Clinical Observation of Employment of Umbilical Cord Derived Mesenchymal Stem Cell for Juvenile Idiopathic Arthritis Therapy*. Stem Cells Int, 2016. 2016: p. 9165267.
60. Alvaro-Gracia, J. M., et al., *Intravenous administration of expanded allogeneic adipose-derived mesenchymal stem cells in refractory rheumatoid arthritis (Cx611): results of a multicentre, dose escalation, randomised, single-blind, placebo-controlled phase Ib/IIa clinical trial*. Ann Rheum Dis, 2016.
61. Van Pham, P., et al., *Isolation and proliferation of umbilical cord tissue derived mesenchymal stem cells for clinical applications*. Cell Tissue Bank, 2015.
62. Fazzina, R., et al., *A new standardized clinical-grade protocol for banking human umbilical cord tissue cells*. Transfusion, 2015. 55(12): p. 2864-73.
63. Bieback, K., *Platelet lysate as replacement for fetal bovine serum in mesenchymal stromal cell cultures*. Transfus Med Hemother, 2013. 40(5): p. 326-35.
64. Stanko, P., et al., *Comparison of human mesenchymal stem cells derived from dental pulp, bone marrow, adipose tissue, and umbilical cord tissue by gene expression*. Biomed Pap Med Fac Univ Palacky Olomouc Czech Repub, 2014. 158(3): p. 373-7.
65. Schira, J., et al., *Significant clinical, neuropathological and behavioural recovery from acute spinal cord trauma by transplantation of a well-defined somatic stem cell from human umbilical cord blood*. Brain, 2012. 135(Pt 2): p. 431-46.
66. Hartmann, I., et al., *Umbilical cord tissue-derived mesenchymal stem cells grow best under GMP-compliant culture conditions and maintain their phenotypic and functional properties*. J Immunol Methods, 2010. 363(1): p. 80-9.

67. Friedman, R., et al., *Umbilical cord mesenchymal stem cells: adjuvants for human cell transplantation*. Biol Blood Marrow Transplant, 2007. 13(12): p. 1477-86.
68. Zhang, X. Y., et al., *Lentiviral vectors for sustained transgene expression in human bone marrow-derived stromal cells*. Mol Ther, 2002. 5(5 Pt 1): p. 555-65.
69. Kyriakou, C. A., et al., *Human mesenchymal stem cells (hMSCs) expressing truncated soluble vascular endothelial growth factor receptor (tsFlk-1) following lentiviral-mediated gene transfer inhibit growth of Burkitt's lymphoma in a murine model*. J Gene Med, 2006. 8(3): p. 253-64.
70. Worsham, D. N., et al., *In vivo gene transfer into adult stem cells in unconditioned mice by in situ delivery of a lentiviral vector*. Mol Ther, 2006. 14(4): p. 514-24.
71. Rabin, N., et al., *A new xenograft model of myeloma bone disease demonstrating the efficacy of human mesenchymal stem cells expressing osteoprotegerin by lentiviral gene transfer*. Leukemia, 2007. 21(10): p. 2181-91.
72. Kallifatidis, G., et al., *Improved lentiviral transduction of human mesenchymal stem cells for therapeutic intervention in pancreatic cancer*. Cancer Gene Ther, 2008. 15(4): p. 231-40.
73. Meyerrose, T. E., et al., *Lentiviral-transduced human mesenchymal stem cells persistently express therapeutic levels of enzyme in a xenotransplantation model of human disease*. Stem Cells, 2008. 26(7): p. 1713-22.
74. McGinley, L., et al., *Lentiviral vector mediated modification of mesenchymal stem cells & enhanced survival in an in vitro model of ischaemia*. Stem Cell Res Ther, 2011. 2(2): p. 12.
75. Liang, X., et al., *Human bone marrow mesenchymal stem cells expressing SDF-1 promote hematopoietic stem cell function of human mobilised peripheral blood CD34+ cells in vivo and in vitro*. Int J Radiat Biol, 2010. 86(3): p. 230-7.
76. Glavaski-Joksimovic, A., et al., *Glial cell line-derived neurotrophic factor-secreting genetically modified human bone marrow-derived mesenchymal stem cells promote recovery in a rat model of Parkinson's disease*. J Neurosci Res, 2010. 88(12): p. 2669-81.
77. Liu, A. M., et al., *Umbilical cord-derived mesenchymal stem cells with forced expression of hepatocyte growth factor enhance remyelination and functional recovery in a rat intracerebral hemorrhage model*. Neurosurgery, 2010. 67(2): p. 357-65; discussion 365-6.
78. Yu, Y. S., et al., *AKT-modified autologous intracoronary mesenchymal stem cells prevent remodeling and repair in swine infarcted myocardium*. Chin Med J (Engl), 2010. 123(13): p. 1702-8.
79. Mueller, L. P., et al., *TRAIL-transduced multipotent mesenchymal stromal cells (TRAIL-MSC) overcome TRAIL resistance in selected CRC cell lines in vitro and in vivo*. Cancer Gene Ther, 2011. 18(4): p. 229-39.
80. Yan, C., et al., *Suppression of orthotopically implanted hepatocarcinoma in mice by umbilical cord-derived mesenchymal stem cells with sTRAIL gene expression driven by AFP promoter*. Biomaterials, 2014. 35(9): p. 3035-43.
81. Deng, Q., et al., *TRAIL-secreting mesenchymal stem cells promote apoptosis in heat-shock-treated liver cancer cells and inhibit tumor growth in nude mice*. Gene Ther, 2014. 21(3): p. 317-27.
82. Sage, E. K., et al., *Systemic but not topical TRAIL-expressing mesenchymal stem cells reduce tumour growth in malignant mesothelioma*. Thorax, 2014. 69(7): p. 638-47.
83. Lian, W. S., et al., *In vivo therapy of myocardial infarction with mesenchymal stem cells modified with prostaglandin I synthase gene improves cardiac performance in mice*. Life Sci, 2011. 88(9-10): p. 455-64.
84. Maijenburg, M. W., et al., *Nuclear receptors Nur77 and Nurr1 modulate mesenchymal stromal cell migration*. Stem Cells Dev, 2012. 21(2): p. 228-38.
85. Harper, M. M., et al., *Transplantation of BDNF-secreting mesenchymal stem cells provides neuroprotection in chronically hypertensive rat eyes*. Invest Ophthalmol Vis Sci, 2011. 52(7): p. 4506-15.
86. Zou, D., et al., *In vitro study of enhanced osteogenesis induced by HIF-1alpha-transduced bone marrow stem cells*. Cell Prolif, 2011. 44(3): p. 234-43.
87. Saito, S., et al., *Mesenchymal stem cells stably transduced with a dominant-negative inhibitor of CCL2 greatly attenuate bleomycin-induced lung damage*. Am J Pathol, 2011. 179(3): p. 1088-94.
88. Seo, K. W., et al., *Anti-tumor effects of canine adipose tissue-derived mesenchymal stromal cell-based interferon-beta gene therapy and cisplatin in a mouse melanoma model*. Cytotherapy, 2011. 13(8): p. 944-55.
89. Yang, H. M., et al., *Enhancement of the immunosuppressive effect of human adipose tissue-derived mesenchymal stromal cells through HLA-G1 expression*. Cytotherapy, 2012. 14(1): p. 70-9.
90. Liang, X. J., et al., *Differentiation of human umbilical cord mesenchymal stem cells into hepatocyte-like cells by hTERT gene transfection in vitro*. Cell Biol Int, 2012. 36(2): p. 215-21.
91. Fei, S., et al., *The antitumor effect of mesenchymal stem cells transduced with a lentiviral vector expressing cytosine deaminase in a rat glioma model*. J Cancer Res Clin Oncol, 2012. 138(2): p. 347-57.
92. Jaganathan, B. G. and D. Bonnet, *Human mesenchymal stromal cells senesce with exogenous OCT4*. Cytotherapy, 2012. 14(9): p. 1054-63.
93. Han, S. H., et al., *Effect of ectopic OCT4 expression on canine adipose tissue-derived mesenchymal stem cell proliferation*. Cell Biol Int, 2014. 38(10): p. 1163-73.
94. Shangguan, L., et al., *Inhibition of TGF-beta/Smad signaling by BAMBI blocks differentiation of human mesenchymal stem cells to carcinoma-associated fibroblasts and abolishes their protumor effects*. Stem Cells, 2012. 30(12): p. 2810-9.
95. Kearns-Jonker, M., et al., *Genetically Engineered Mesenchymal Stem Cells Influence Gene Expression in Donor Cardiomyocytes and the Recipient Heart*. J Stem Cell Res Ther, 2012. S1.
96. Ma, G. L., et al., *[Study of inhibiting and killing effects of transgenic LIGHT human umbilical cord blood mesenchymal stem cells on stomach cancer]*. Zhonghua Wei Chang Wai Ke Za Zhi, 2012. 15(11): p. 1178-81.
97. Huang, F., et al., *Mesenchymal stem cells modified with miR-126 release angiogenic factors and activate Notch ligand Delta-like-4, enhancing ischemic angiogenesis and cell survival*. Int J Mol Med, 2013. 31(2): p. 484-92.
98. Huang, F., et al., *Overexpression of miR-126 promotes the differentiation of mesenchymal stem cells toward endothelial cells via activation of PI3K/Akt and MAPK/ERK pathways and release of paracrine factors*. Biol Chem, 2013. 394(9): p. 1223-33.
99. Fang, Z., et al., *Differentiation of GFP-Bcl-2-engineered mesenchymal stem cells towards a nucleus pulposus-like phenotype under hypoxia in vitro*. Biochem Biophys Res Commun, 2013. 432(3): p. 444-50.

100. Madonna, R., et al., *Transplantation of mesenchymal cells rejuvenated by the overexpression of telomerase and myocardin promotes revascularization and tissue repair in a murine model of hindlimb ischemia.* Circ Res, 2013. 113(7): p. 902-14.

101. Zang, Y., et al., *[Influence of CXCR4 overexpressed mesenchymal stem cells on hematopoietic recovery of irradiated mice].* Zhongguo Shi Yan Xue Ye Xue Za Zhi, 2013. 21(5): p. 1261-5.

102. Cao, Z., et al., *Protective effects of mesenchymal stem cells with CXCR4 up-regulation in a rat renal transplantation model.* PLoS One, 2013. 8(12): p. e82949.

103. Liu, S., et al., *Overexpression of Wnt11 promotes chondrogenic differentiation of bone marrow-derived mesenchymal stem cells in synergism with TGF-beta.* Mol Cell Biochem, 2014. 390(1-2): p. 123-31.

104. Zhu, Y., et al., *Mesenchymal stem cell-based NK4 gene therapy in nude mice bearing gastric cancer xenografts.* Drug Des Devel Ther, 2014. 8: p. 2449-62.

105. Yu, B., et al., *Enhanced mesenchymal stem cell survival induced by GATA-4 overexpression is partially mediated by regulation of the miR-15 family.* Int J Biochem Cell Biol, 2013. 45(12): p. 2724-35.

106. Xu, W., et al., *Basic fibroblast growth factor expression is implicated in mesenchymal stem cells response to light-induced retinal injury.* Cell Mol Neurobiol, 2013. 33(8): p. 1171-9.

107. Li, W., et al., *Bcl-2 engineered MSCs inhibited apoptosis and improved heart function.* Stem Cells, 2007. 25(8): p. 2118-27.

108. Tsubokawa, T., et al., *Impact of anti-apoptotic and anti-oxidative effects of bone marrow mesenchymal stem cells with transient overexpression of heme oxygenase-1 on myocardial ischemia.* Am J Physiol Heart Circ Physiol, 2010. 298(5): p. H1320-9.

109. Zhou, H., et al., *Exendin-4 protects adipose-derived mesenchymal stem cells from apoptosis induced by hydrogen peroxide through the PI3K/Akt-Sfrp2 pathways.* Free Radic Biol Med, 2014. 77: p. 363-75.

110. Le Blanc, K., et al., *Treatment of severe acute graft-versus-host disease with third party haploidentical mesenchymal stem cells.* Lancet, 2004. 363(9419): p. 1439-41.

111. Lazarus, H. M., et al., *Cotransplantation of HLA-identical sibling culture-expanded mesenchymal stem cells and hematopoietic stem cells in hematologic malignancy patients.* Biol Blood Marrow Transplant, 2005. 11(5): p. 389-98.

112. Bernardo, M. E., et al., *Optimization of in vitro expansion of human multipotent mesenchymal stromal cells for cell-therapy approaches: further insights in the search for a fetal calf serum substitute.* J Cell Physiol, 2007. 211(1): p. 121-30.

113. Reinisch, A., et al., *Humanized system to propagate cord blood-derived multipotent mesenchymal stromal cells for clinical application.* Regen Med, 2007. 2(4): p. 371-82.

114. Capelli, C., et al., *Human platelet lysate allows expansion and clinical grade production of mesenchymal stromal cells from small samples of bone marrow aspirates or marrow filter washouts.* Bone Marrow Transplant, 2007. 40(8): p. 785-91.

115. Lataillade, J. J., et al., *New approach to radiation burn treatment by dosimetry-guided surgery combined with autologous mesenchymal stem cell therapy.* Regen Med, 2007. 2(5): p. 785-94.

116. Seshareddy, K., D. Troyer, and M. L. Weiss, *Method to isolate mesenchymal-like cells from Wharton's Jelly of umbilical cord.* Methods Cell Biol, 2008. 86: p. 101-19.

117. Sensebe, L., *Clinical grade production of mesenchymal stem cells.* Biomed Mater Eng, 2008. 18(1 Suppl): p. S3-10.

118. Sotiropoulou, P. A., S. A. Perez, and M. Papamichail, *Clinical grade expansion of human bone marrow mesenchymal stem cells.* Methods Mol Biol, 2007. 407: p. 245-63.

119. Shetty, P., et al., *Clinical grade mesenchymal stem cells transdifferentiated under xenofree conditions alleviates motor deficiencies in a rat model of Parkinson's disease.* Cell Biol Int, 2009. 33(8): p. 830-8.

120. Zhang, X., et al., *Cotransplantation of HLA-identical mesenchymal stem cells and hematopoietic stem cells in Chinese patients with hematologic diseases.* Int J Lab Hematol, 2010. 32(2): p. 256-64.

121. Arrigoni, E., et al., *Isolation, characterization and osteogenic differentiation of adipose-derived stem cells: from small to large animal models.* Cell Tissue Res, 2009. 338(3): p. 401-11.

122. Grisendi, G., et al., *GMP-manufactured density gradient media for optimized mesenchymal stromal/stem cell isolation and expansion.* Cytotherapy, 2010. 12(4): p. 466-77.

123. Prasad, V. K., et al., *Efficacy and safety of ex vivo cultured adult human mesenchymal stem cells (Prochymal) in pediatric patients with severe refractory acute graft-versus-host disease in a compassionate use study.* Biol Blood Marrow Transplant, 2011. 17(4): p. 534-41.

124. Sensebe, L., P. Bourin, and K. Tarte, *Good manufacturing practices production of mesenchymal stem/stromal cells.* Hum Gene Ther, 2011. 22(1): p. 19-26.

125. Capelli, C., et al., *Minimally manipulated whole human umbilical cord is a rich source of clinical-grade human mesenchymal stromal cells expanded in human platelet lysate.* Cytotherapy, 2011. 13(7): p. 786-801.

126. Ilic, N., et al., *Manufacture of clinical grade human placenta-derived multipotent mesenchymal stromal cells.* Methods Mol Biol, 2011. 698: p. 89-106.

127. Santos, F., et al., *Toward a clinical-grade expansion of mesenchymal stem cells from human sources: a microcarrier-based culture system under xeno-free conditions.* Tissue Eng Part C Methods, 2011. 17(12): p. 1201-10.

128. Timmins, N. E., et al., *Closed system isolation and scalable expansion of human placental mesenchymal stem cells.* Biotechnol Bioeng, 2012. 109(7): p. 1817-26.

129. Warnke, P. H., et al., *A clinically feasible protocol for using human platelet lysate and mesenchymal stem cells in regenerative therapies.* J Craniomaxillofac Surg, 2013. 41(2): p. 153-61.

130. Fekete, N., et al., *GMP-compliant isolation and large-scale expansion of bone marrow-derived MSC.* PLoS One, 2012. 7(8): p. e43255.

131. Hanley, P. J., et al., *Manufacturing mesenchymal stromal cells for phase I clinical trials.* Cytotherapy, 2013. 15(4): p. 416-22.

132. Trojahn Kolle, S. F., et al., *Pooled human platelet lysate versus fetal bovine serum-investigating the proliferation rate, chromosome stability and angiogenic potential of human adipose tissue-derived stem cells intended for clinical use.* Cytotherapy, 2013. 15(9): p. 1086-97.

133. Veronesi, E., et al., *Transportation conditions for prompt use of ex vivo expanded and freshly harvested*

133. *clinical-grade bone marrow mesenchymal stromal/stem cells for bone regeneration.* Tissue Eng Part C Methods, 2014. 20(3): p. 239-51.
134. Dolley-Sonneville, P. J., L. E. Romeo, and Z. K. Melkoumian, *Synthetic surface for expansion of human mesenchymal stem cells in xeno-free, chemically defined culture conditions.* PLoS One, 2013. 8(8): p. e70263.
135. Siciliano, C., et al., *Optimization of the isolation and expansion method of human mediastinal-adipose tissue derived mesenchymal stem cells with virally inactivated GMP-grade platelet lysate.* Cytotechnology, 2015. 67(1): p. 165-74.
136. Martins, J. P., et al., *Towards an advanced therapy medicinal product based on mesenchymal stromal cells isolated from the umbilical cord tissue: quality and safety data.* Stem Cell Res Ther, 2014. 5(1): p. 9.
137. Iudicone, P., et al., *Pathogen-free, plasma-poor platelet lysate and expansion of human mesenchymal stem cells.* J Transl Med, 2014. 12: p. 28.
138. Skrahin, A., et al., *Autologous mesenchymal stromal cell infusion as adjunct treatment in patients with multidrug and extensively drug-resistant tuberculosis: an open-label phase 1 safety trial.* Lancet Respir Med, 2014. 2(2): p. 108-22.
139. Ikebe, C. and K. Suzuki, *Mesenchymal stem cells for regenerative therapy: optimization of cell preparation protocols.* Biomed Res Int, 2014. 2014: p. 951512.
140. Chatzistamatiou, T. K., et al., *Optimizing isolation culture and freezing methods to preserve Wharton's jelly's mesenchymal stem cell (MSC) properties: an MSC banking protocol validation for the Hellenic Cord Blood Bank.* Transfusion, 2014. 54(12): p. 3108-20.
141. Swamynathan, P., et al., *Are serum free and xeno-free culture conditions ideal for large scale clinical grade expansion of Wharton's jelly derived mesenchymal stem cells? A comparative study.* Stem Cell Res Ther, 2014. 5(4): p. 88.
142. Vaes, B., et al., *Culturing protocols for human multipotent adult stem cells.* Methods Mol Biol, 2015. 1235: p. 49-58.
143. Devito, L., et al., *Wharton's jelly mesenchymal stromal/stem cells derived under chemically defined animal product-free low oxygen conditions are rich in MSCA-1(+) subpopulation.* Regen Med, 2014. 9(6): p. 723-32.
144. Andreu, Z. and M. Yanez-Mo, *Tetraspanins in extracellular vesicle formation and function.* Front Immunol, 2014. 5: p. 442.
145. Pols, M. S. and J. Klumperman, *Trafficking and function of the tetraspanin CD63.* Exp Cell Res, 2009. 315(9): p. 1584-92.
146. Hemler, M. E., *Tetraspanin proteins mediate cellular penetration, invasion, and fusion events and define a novel type of membrane microdomain.* Annu Rev Cell Dev Biol, 2003. 19: p. 397-422.
147. Ahmadi, M., et al., *Bone marrow mesenchymal stem cells and their conditioned media could potentially ameliorate ovalbumin-induced asthmatic changes.* Biomed Pharmacother, 2016. 85: p. 28-40.
148. Nemunaitis, J., et al., *Human marrow stromal cells: response to interleukin-6 (IL-6) and control of IL-6 expression.* Blood, 1989. 74(6): p. 1929-35.
149. Sadovnikova, E. Y., et al., *Induction of hematopoietic microenvironment by the extracellular matrix from long-term bone marrow cultures.* Ann Hematol, 1991. 62(5): p. 160-4.
150. Lazarus, H. M., et al., *Ex vivo expansion and subsequent infusion of human bone marrow-derived stromal progenitor cells (mesenchymal progenitor cells): implications for therapeutic use.* Bone Marrow Transplant, 1995. 16(4): p. 557-64.
151. Yoo, J. U., et al., *The chondrogenic potential of human bone-marrow-derived mesenchymal progenitor cells.* J Bone Joint Surg Am, 1998. 80(12): p. 1745-57.
152. Fleming, J. E., Jr., et al., *Monoclonal antibody against adult marrow-derived mesenchymal stem cells recognizes developing vasculature in embryonic human skin.* Dev Dyn, 1998. 212(1): p. 119-32.
153. Ghilzon, R., C. A. McCulloch, and R. Zohar, *Stromal mesenchymal progenitor cells.* Leuk Lymphoma, 1999. 32(3-4): p. 211-21.
154. De Cesaris, V., et al., *Isolation, proliferation and characterization of endometrial canine stem cells.* Reprod Domest Anim, 2016.
155. Van Pham, P., et al., *Isolation and proliferation of umbilical cord tissue derived mesenchymal stem cells for clinical applications.* Cell Tissue Bank, 2016. 17(2): p. 289-302.
156. Zhao, G., et al., *Large-scale expansion of Wharton's jelly-derived mesenchymal stem cells on gelatin microbeads, with retention of self-renewal and multipotency characteristics and the capacity for enhancing skin wound healing.* Stem Cell Res Ther, 2015. 6: p. 38.
157. Huang, P., et al., *Differentiation of human umbilical cord Wharton's jelly-derived mesenchymal stem cells into germ-like cells in vitro.* J Cell Biochem, 2010. 109(4): p. 747-54.
158. Wang, S. J., et al., *Chondrogenic Potential of Peripheral Blood Derived Mesenchymal Stem Cells Seeded on Demineralized Cancellous Bone Scaffolds.* Sci Rep, 2016. 6: p. 36400.
159. Fazeli, Z., M. D. Omrani, and S. M. Ghaderian, *CD29/CD184 expression analysis provides a signature for identification of neuronal like cells differentiated from PBMSCs.* Neurosci Lett, 2016. 630: p. 189-93.
160. Wu, G., et al., *Osteogenesis of peripheral blood mesenchymal stem cells in self assembling peptide nanofiber for healing critical size calvarial bony defect.* Sci Rep, 2015. 5: p. 16681.
161. Shaer, A., et al., *Isolation and characterization of Human Mesenchymal Stromal Cells Derived from Placental Decidua Basalis; Umbilical cord Wharton's Jelly and Amniotic Membrane.* Pak J Med Sci, 2014. 30(5): p. 1022-6.
162. Fu, W. L., C. Y. Zhou, and J. K. Yu, *A new source of mesenchymal stem cells for articular cartilage repair: MSCs derived from mobilized peripheral blood share similar biological characteristics in vitro and chondrogenesis in vivo as MSCs from bone marrow in a rabbit model.* Am J Sports Med, 2014. 42(3): p. 592-601.
163. El-Badawy, A., et al., *Adipose Stem Cells Display Higher Regenerative Capacities and More Adaptable Electro-Kinetic Properties Compared to Bone Marrow-Derived Mesenchymal Stromal Cells.* Sci Rep, 2016. 6: p. 37801.
164. Plock, J. A., et al., *The Influence of Timing and Frequency of Adipose-Derived Mesenchymal Stem Cell Therapy on Immunomodulation Outcomes After Vascularized Composite Allotransplantation.* Transplantation, 2017. 101(1): p. e1-e11.
165. Shin, T. H., et al., *Human umbilical cord blood-stem cells direct macrophage polarization and block inflammasome activation to alleviate rheumatoid arthritis.* Cell Death Dis, 2016. 7(12): p. e2524.

The invention claimed is:

1. A method of treating rheumatoid arthritis comprising:
identifying a patient suffering from rheumatoid arthritis;
obtaining a group of mesenchymal stem cells;
identifying expression of one or more markers selected from the group consisting of: TNFR-1, ENA-78, and IGFBP-3;
selecting cells that express higher levels, compared to normal MSCs, of one or more proteins selected from the group consisting of TNFR-1, ENA-78, and IGFBP-3;
administering said selected cells to said patient in an amount sufficient to treat said rheumatoid arthritis.

2. The method of claim 1, wherein said mesenchymal stem cells are selected based on expression of a marker selected from the group consisting of: a) CD73; b) CD90; and c) CD105.

3. The method of claim 1, wherein said mesenchymal stem cells lack expression of a marker selected from the group consisting of: a) CD14; b) CD45; and c) CD34.

4. The method of claim 1 wherein said mesenchymal stem cells are derived from umbilical cord tissue and express a marker selected from the group consisting of: a) CD10; b) CD13; c) CD44; d) CD73; and e) CD90.

5. The method of claim 1, wherein the marker is TNFR-1.

6. The method of claim 5, wherein the level of TNFR-1 is greater than 20.4 pg/ML.

7. The method of claim 1, wherein the marker is ENA-78.

8. The method of claim 7, wherein the level of ENA-78 is greater than 16.31 pg/ML.

9. The method of claim 1, wherein the marker is IGFBP-3.

10. The method of claim 9, wherein the level of IGFBP-3 is greater than 46.50 pg/ML.

* * * * *